(12) United States Patent
Endo

(10) Patent No.: US 10,959,606 B2
(45) Date of Patent: Mar. 30, 2021

(54) ENDOSCOPE SYSTEM AND GENERATING EMPHASIZED IMAGE BASED ON COLOR INFORMATION

(71) Applicant: FUJIFILM Corporation, Tokyo (JP)

(72) Inventor: Maiko Endo, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 382 days.

(21) Appl. No.: 15/936,466

(22) Filed: Mar. 27, 2018

(65) Prior Publication Data

US 2018/0214009 A1    Aug. 2, 2018

Related U.S. Application Data

(63) Continuation of application No. PCT/JP2016/078514, filed on Sep. 27, 2016.

(30) Foreign Application Priority Data

Sep. 28, 2015    (JP) .............................. JP2015-190150

(51) Int. Cl.
*A61B 1/313* (2006.01)
*A61B 1/00* (2006.01)
(Continued)

(52) U.S. Cl.
CPC ...... *A61B 1/00186* (2013.01); *A61B 1/00009* (2013.01); *A61B 1/00059* (2013.01);
(Continued)

(58) Field of Classification Search
CPC combination set(s) only.
See application file for complete search history.

(56) References Cited

U.S. PATENT DOCUMENTS

| 6,996,260 B1 * | 2/2006 | Skands | A61B 3/12 382/128 |
| 7,492,934 B2 * | 2/2009 | Mundy | A61B 6/5217 382/128 |

(Continued)

FOREIGN PATENT DOCUMENTS

| EP | 2733669 | 5/2014 |
| JP | H02279131 | 11/1990 |

(Continued)

OTHER PUBLICATIONS

"Office Action of Japan Counterpart Application", dated Apr. 7, 2020, with English translation thereof, p. 1-p. 8.

(Continued)

*Primary Examiner* — John P Leubecker
*Assistant Examiner* — Shankar Raj Ghimire
(74) *Attorney, Agent, or Firm* — JCIPRNET

(57) ABSTRACT

The image acquisition unit acquires an image captured by an endoscope. The extraction unit extracts a blood vessel of an observation target. The index value calculation unit calculates a plurality of blood vessel index values based on the blood vessel. The determination unit determines whether each of the plurality of blood vessel index values is a normal value or an abnormal value. The color information setting unit sets color information for an abnormal index value, which is the blood vessel index value determined to be the abnormal value by the determination unit, or sets color information for a normal index value, which is the blood vessel index value determined to be the normal value by the determination unit. The image generation unit generates an emphasized image, in which the blood vessel is emphasized, based on the color information.

10 Claims, 12 Drawing Sheets

(51) Int. Cl.
*A61B 1/06* (2006.01)
*A61B 1/04* (2006.01)
*A61B 1/05* (2006.01)
*A61B 5/00* (2006.01)

(52) U.S. Cl.
CPC .......... *A61B 1/00188* (2013.01); *A61B 1/063* (2013.01); *A61B 1/0638* (2013.01); *A61B 1/3137* (2013.01); *A61B 1/00006* (2013.01); *A61B 1/041* (2013.01); *A61B 1/043* (2013.01); *A61B 1/05* (2013.01); *A61B 1/0684* (2013.01); *A61B 5/0084* (2013.01); *G06T 2207/10068* (2013.01); *G06T 2207/10152* (2013.01); *G06T 2207/30101* (2013.01)

(56) References Cited

U.S. PATENT DOCUMENTS

| | | | | |
|---|---|---|---|---|
| 7,546,154 | B2* | 6/2009 | Hornegger | G06T 7/0012 382/128 |
| 8,913,111 | B2 | 12/2014 | Takahashi | |
| 9,814,375 | B2 | 11/2017 | Daidoji et al. | |
| 2002/0086347 | A1* | 7/2002 | Johnson | A61B 5/02007 435/40.5 |
| 2003/0050553 | A1* | 3/2003 | Samoszuk | A61B 5/0059 600/410 |
| 2004/0171932 | A1* | 9/2004 | Raman | A61B 6/504 600/425 |
| 2009/0005693 | A1* | 1/2009 | Brauner | G06T 7/62 600/481 |
| 2009/0148017 | A1* | 6/2009 | Inoue | A61B 1/04 382/128 |
| 2010/0159497 | A1* | 6/2010 | Kimia | G06T 7/44 435/29 |
| 2011/0077462 | A1* | 3/2011 | Saitou | A61B 1/063 600/109 |
| 2011/0170759 | A1* | 7/2011 | Bjornerud | G06T 7/0012 382/131 |
| 2011/0237915 | A1* | 9/2011 | Yamaguchi | A61B 5/14551 600/339 |
| 2011/0245642 | A1* | 10/2011 | Minetoma | A61B 5/0084 600/324 |
| 2011/0319711 | A1* | 12/2011 | Yamaguchi | A61B 5/14551 600/109 |
| 2012/0083696 | A1* | 4/2012 | Kitamura | G06T 7/33 600/443 |
| 2012/0327205 | A1* | 12/2012 | Takahashi | G02B 23/2461 348/65 |
| 2013/0018242 | A1* | 1/2013 | Yamaguchi | A61B 5/0084 600/339 |
| 2015/0327755 | A1 | 11/2015 | Daidoji et al. | |
| 2016/0014328 | A1 | 1/2016 | Rokutanda | |
| 2017/0100029 | A1* | 4/2017 | Faber | A61B 5/6821 |
| 2017/0112357 | A1* | 4/2017 | Kono | A61B 1/3137 |

FOREIGN PATENT DOCUMENTS

| | | |
|---|---|---|
| JP | 2009066301 | 4/2009 |
| JP | 2010268961 | 12/2010 |
| JP | 2011135983 | 7/2011 |
| JP | 2011217798 | 11/2011 |
| JP | 2011218135 | 11/2011 |
| JP | 2013116353 | 6/2013 |
| JP | 2014144144 | 8/2014 |
| JP | 2014230647 | 12/2014 |
| WO | 2014155782 | 10/2014 |

OTHER PUBLICATIONS

"International Search Report (Form PCT/ISA/210) of PCT/JP2016/078514," dated Dec. 13, 2016, with English translation thereof, pp. 1-4.

"Written Opinion of the International Searching Authority (Form PCT/ISA/237) of PCT/JP2016/078514," dated Dec. 13, 2016, with English translation thereof, pp. 1-8.

"Search Report of Europe Counterpart Application", dated Sep. 3, 2018, p. 1-p. 8.

* cited by examiner

ENDOSCOPE SYSTEM AND GENERATING EMPHASIZED IMAGE BASED ON COLOR INFORMATION

CROSS-REFERENCE TO RELATED APPLICATIONS

This application is a Continuation of PCT International Application No. PCT/JP2016/078514 filed on Sep. 27, 2016, which claims priority under 35 U.S.C. § 119(a) to Japanese Patent Application No. 2015-190150 filed on Sep. 28, 2015. The above application is hereby expressly incorporated by reference, in its entirety, into the present application.

BACKGROUND OF THE INVENTION

1. Field of the Invention

The present invention relates to an endoscope system for generating an image obtained by imaging an observation target in a subject and an operation method of an endoscope system.

2. Description of the Related Art

In the medical field, diagnosis using an endoscope system including a light source device, an endoscope, and a processor device has been widely performed. In the endoscope system, illumination light from the light source device is emitted to an observation target through the endoscope, and the processor device generates an image of the observation target based on an image signal obtained by imaging the observation target illuminated with the illumination light. By displaying the image on a monitor, a doctor can perform diagnosis while observing the image on the monitor.

In the diagnosis using the endoscope system, in addition to displaying an image in which the observation target is expressed with a natural color shade using white illumination light (hereinafter, referred to as a normal observation image) on the monitor, for example, by displaying on the monitor an image colored according to the depth or density of a blood vessel of the observation target (hereinafter, referred to as a special observation image) as disclosed in JP2011-217798A (corresponding to US 2011/0245642A1) or a special observation image colored according to a change in blood volume or oxygen saturation as disclosed in JP1990-279131A (JP-H02-279131A), diagnosis is done for the purpose of observing information regarding blood vessels.

SUMMARY OF THE INVENTION

An index value obtained by digitizing information regarding blood vessels, such as the depth or density of a blood vessel, is useful information for diagnosis. However, a doctor makes determinations by considering a plurality of index values comprehensively in many cases. For this reason, in the case of displaying a plurality of index values with coloring as disclosed in JP2011-217798A and JP1990-279131A (JP-H02-279131A), the doctor may hesitate to make a determination due to a large amount of information. Therefore, even in the case of performing diagnosis using a plurality of index values, it has been required to narrow down the range to index values that are to be noticed upon diagnosis and present the index values.

It is an object of the present invention to provide an endoscope system capable of narrowing down the range to index values that are to be noticed upon diagnosis and presenting the index values even in a case where a plurality of index values are used and an operation method of an endoscope system.

An endoscope system of the present invention comprises an image acquisition unit, an extraction unit, an index value calculation unit, a determination unit, a color information setting unit, and an image generation unit. The image acquisition unit acquires an image obtained by imaging an observation target with an endoscope. The extraction unit extracts a structure included in the observation target from the image. The index value calculation unit calculates a plurality of index values based on the structure extracted by the extraction unit. The determination unit determines whether each of the plurality of index values is a normal value indicating a normal state or an abnormal value different from the normal value. The color information setting unit sets color information for an abnormal index value, which is the index value determined to be the abnormal value by the determination unit, or sets color information for a normal index value, which is the index value determined to be the normal value by the determination unit. The image generation unit generates an emphasized image, in which the structure is emphasized, based on the color information set by the color information setting unit.

It is preferable that the determination unit performs the determination by comparing the index value with a specific threshold value or performs the determination with reference to a look-up table that stores to which of the normal value and the abnormal value the index value corresponds.

It is preferable that the structure is a blood vessel.

It is preferable that the color information is a plurality of pieces of information and a priority is set for each of the pieces of color information, there are a plurality of the abnormal index values or a plurality of the normal index values and a priority is set for each of the plurality of abnormal index values or the plurality of normal index values, and the color information setting unit assigns the color information having a higher priority to the abnormal index value or the normal index value having a higher priority among the abnormal index values or the normal index values.

It is preferable to further comprise a priority changing unit that changes a priority set for each of the abnormal index values or the normal index values based on observation conditions. It is preferable that the color information setting unit performs the assignment according to a changed priority.

It is preferable to further comprise an endoscope identification unit that identifies whether the endoscope is an upper observation endoscope or a lower observation endoscope. It is preferable that in a case where replacement between the upper observation endoscope and the lower observation endoscope is performed as the observation conditions, the priority changing unit changes a priority of each of the abnormal index values or the normal index values.

It is preferable that in a case where an observation distance from the observation target is changed from a first observation distance to a second observation distance different from the first observation distance as the observation conditions, the priority changing unit changes a priority of each of the abnormal index values or the normal index values.

It is preferable to further comprise a zoom operation unit that changes a zoom magnification of the endoscope between a first zoom magnification and a second zoom magnification different from the first zoom magnification. It is preferable that in a case where the first zoom magnification is changed to the second zoom magnification as the observation conditions, the priority changing unit changes a priority of each of the abnormal index values or the normal index values.

It is preferable to further comprise a mode operation unit that selects one observation mode from a plurality of observation modes in which two or more of the plurality of index values are used and sets a priority based on diagnostics for each of the index values used in the selected observation mode. It is preferable that a priority is set for each of the abnormal index values or the normal index values based on the priority set for each of the index values. It is preferable that in a case where the observation mode is switched from a first observation mode to a second observation mode different from the first observation mode as the observation conditions, the priority changing unit changes a priority of each of the abnormal index values or the normal index values.

It is preferable that in a case where a specific coloring agent is sprayed on the observation target as the observation conditions, the priority changing unit changes a priority of each of the abnormal index values or the normal index values.

It is preferable to further comprise a normal index value storage unit that stores the normal index value and a brightness information setting unit that calculates a difference value between the abnormal index value and the normal index value and sets brightness information according to the difference value. It is preferable that the image generation unit generates the emphasized image based on the set color information and the set brightness information.

An operation method of an endoscope system of the present invention comprises: a step in which an image acquisition unit acquires an image obtained by imaging an observation target with an endoscope; a step in which an extraction unit extracts a structure included in the observation target from the image; a step in which an index value calculation unit calculates a plurality of index values based on the structure extracted by the extraction unit; a step in which a determination unit determines whether each of the plurality of index values is a normal value indicating a normal state or an abnormal value different from the normal value; a step in which a color information setting unit sets color information for an abnormal index value, which is the index value determined to be the abnormal value by the determination unit, or sets color information for a normal index value, which is the index value determined to be the normal value by the determination unit; and a step in which an image generation unit generates an emphasized image, in which the structure is emphasized, based on the color information set by the color information setting unit.

It is preferable that the determination unit performs the determination by comparing the index value with a specific threshold value or performs the determination with reference to a look-up table that stores to which of the normal value and the abnormal value the index value corresponds.

According to the endoscope system and the operation method of an endoscope system of the present invention, even in a case where a plurality of index values are used, it is possible to narrow down the range to index values that are to be noticed upon diagnosis and present the index values.

DESCRIPTION OF THE PREFERRED EMBODIMENTS

First Embodiment

Figure 1:
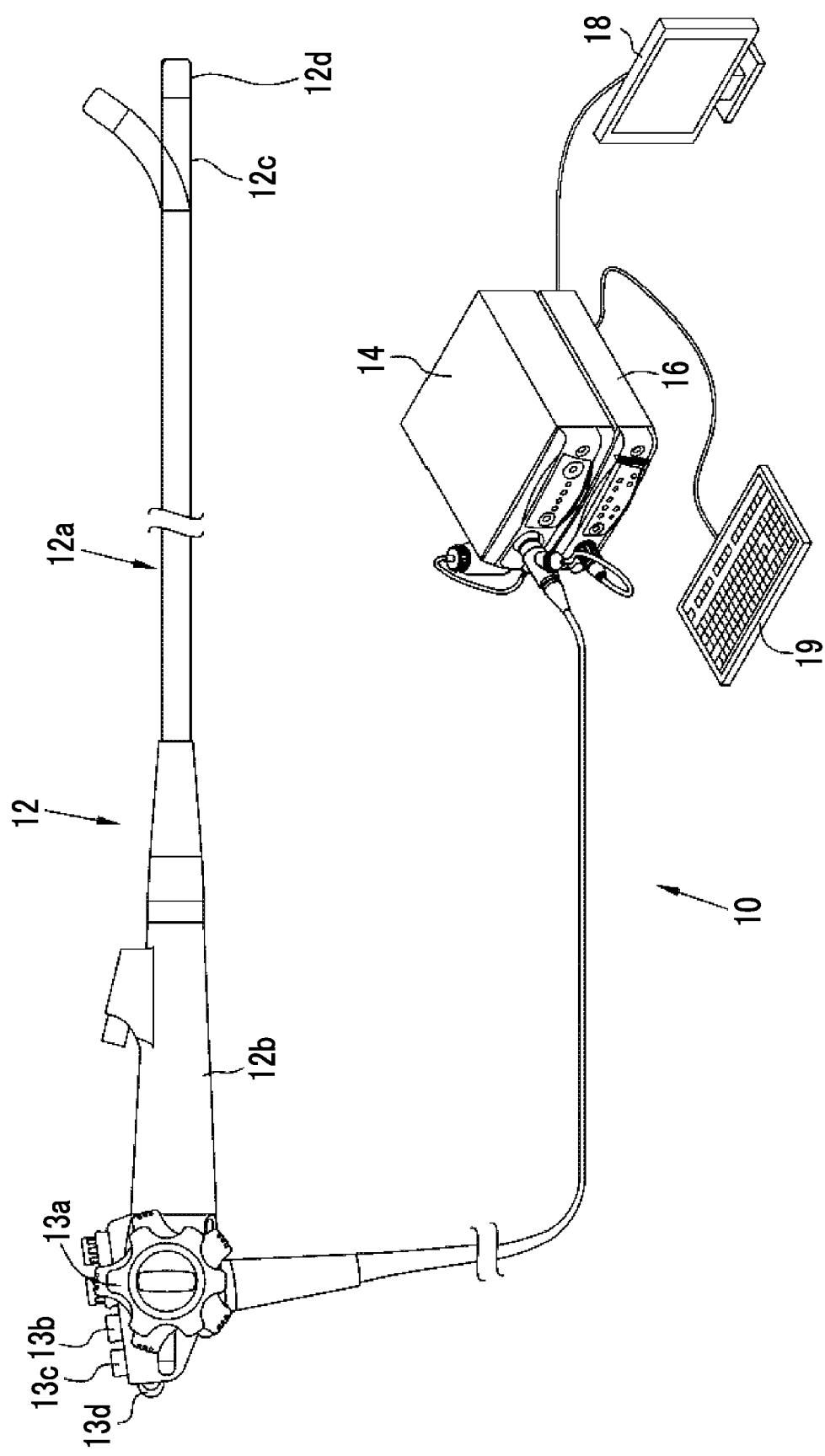
FIG. 1 is an external view of an endoscope system of a first embodiment.

As shown in FIG. 1, an endoscope system 10 includes an endoscope 12, a light source device 14, a processor device 16, a monitor 18, and a console 19. The endoscope 12 is optically connected to the light source device 14, and is electrically connected to the processor device 16. The endoscope 12 includes an insertion part 12a that is inserted into a subject, an operation unit 12b provided in a proximal end portion of the insertion part 12a, and a bending portion 12c and a distal end portion 12d that are provided on the distal end side of the insertion part 12a. By operating an angle knob 13a of the operation unit 12b, the bending portion 12c is bent. Through the bending operation, the distal end portion 12d is directed in a desired direction.

In addition to the angle knob 13a, a still image acquisition unit 13b used for a still image acquisition operation, a mode switching unit 13c used for an observation mode switching operation, and a zoom operation unit 13d used for a zoom magnification change operation are provided in the operation unit 12b. The still image acquisition unit 13b enables a freeze operation for displaying a still image of the observation target on the monitor 18 and a release operation for storing the still image in a storage.

The endoscope system 10 has a normal mode and a special mode as observation modes. In a case where the observation mode is a normal mode, the light source device 14 emits almost white light (hereinafter, referred to as white light) as illumination light. In a case where the observation mode is a special mode, the light source device 14 emits light having a specific wavelength range (hereinafter, referred to as narrowband light), which is narrower than the wavelength range of the white light, as illumination light.

The processor device 16 is electrically connected to the monitor 18 and the console 19. The monitor 18 outputs and displays an image of the observation target, information attached to the image, and the like. The console 19 functions as a user interface for receiving an input operation, such as designation of a region of interest (ROI) or function setting.

Figure 2:
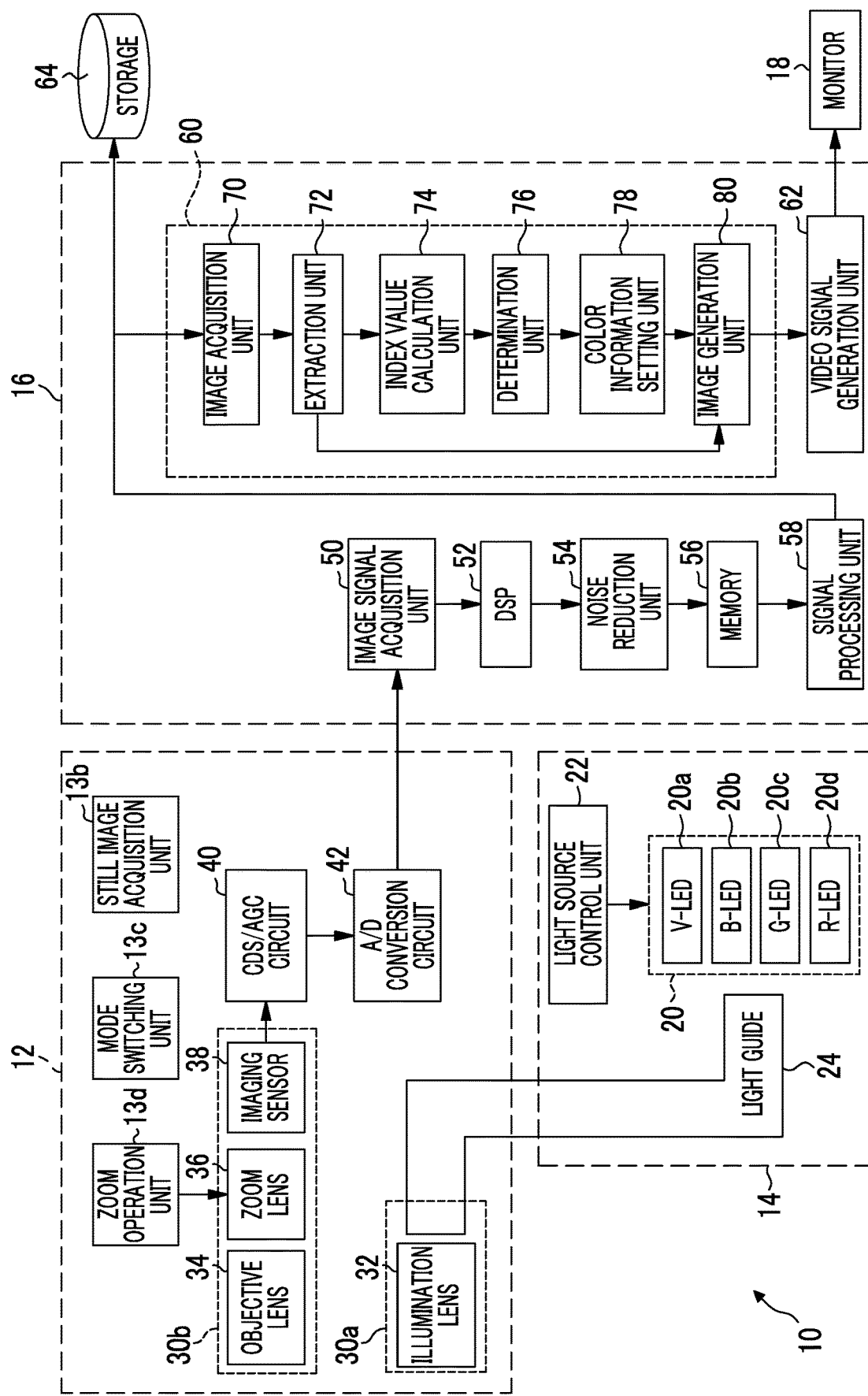
FIG. 2 is a block diagram showing a function of the endoscope system.

As shown in FIG. 2, the light source device 14 includes a light source 20 that emits illumination light used for illumination of the observation target and a light source control unit 22 that controls the light source 20. The light source 20 is, for example, a semiconductor light source such as a light emitting diode (LED) of a plurality of colors, a combination of a laser diode and a phosphor, or a xenon lamp. The light source 20 includes an optical filter for adjusting the wavelength range of light emitted from the LED or the like. The light source control unit 22 controls the emission amount of illumination light by ON/OFF of the LED or the like or by adjusting the driving current or the driving voltage of the LED or the like. In addition, the light source control unit 22 controls the wavelength range of illumination light by changing the optical filter or the like.

In the present embodiment, the light source 20 is configured to include a plurality of light sources having different wavelength ranges. For example, the light source 20 has LEDs of four colors of a violet light emitting diode (V-LED) 20a, a blue light emitting diode (B-LED) 20b, a green light emitting diode (G-LED) 20c, and a red light emitting diode (R-LED) 20d. The V-LED 20a emits violet light V in a wavelength range of 380 nm to 420 nm. The B-LED 20b emits blue light B in a wavelength range of 420 nm to 500 nm. The G-LED 20c emits green light G in a wavelength range of 480 nm to 600 nm. The R-LED 20d emits red light R in a wavelength range of 600 nm to 650 nm. The center wavelengths and the peak wavelengths of light beams of the respective colors may be the same or different from each other.

The light source control unit 22 adjusts the emission timing, emission period, amount, and spectrum of illumination light by independently controlling ON/OFF of each of the LEDs 20a to 20d, the light emission amount at the time of lighting. The ON/OFF control of the light source control unit 22 is different for each observation mode. In the case of the normal mode, the light source control unit 22 turns on all of the V-LED 20a, the B-LED 20b, the G-LED 20c, and the R-LED 20d. Therefore, in the normal mode, the light source 20 emits white light including the violet light V, the blue light B, the green light G, and the red light R.

In the case of the special mode, the light source control unit 22 switches between the control of turning on only the V-LED 20a and the control of turning on only the B-LED 20b. Therefore, in the special mode, the light source 20 sequentially emits the violet light V and the blue light B. In a case where the violet light V and the blue light B are used as illumination light, it is possible to observe a range from a relatively shallow submucosal position (hereinafter, referred to as a surface layer) to a shallower position (hereinafter, referred to as an extremely surface layer) than the surface layer. Since the wavelength of the purple light V is shorter than that of the blue light B, the degree of penetration into the observation target is low, and only blood vessels in the extremely surface layer (hereinafter referred to as extremely superficial blood vessels) are projected. Instead, the contrast of the extremely superficial blood vessel is higher than that in the case of using the blue light B. The contrast is, for example, a ratio of the amount of reflected light from the surrounding mucous membrane to the amount of reflected light from the blood vessel. On the other hand, since the wavelength of the blue light B is longer than that of the violet light V, the degree of penetration into the observation target is high, and only blood vessels in the surface layer (hereinafter referred to as superficial blood vessels) are projected. Instead, the contrast of the extremely superficial blood vessel is lower than that in the case of using the violet light V.

The illumination light emitted from the light source 20 is incident on a light guide 24 inserted into the insertion part 12a through an optical path coupling portion (not shown) formed by a mirror and/or a lens. The light guide 24 is built into the endoscope 12 and a universal cord, and propagates the illumination light to the distal end portion 12d of the endoscope 12. The universal cord is a cord for connecting the endoscope 12 with the light source device 14 and the processor device 16. As the light guide 24, it is possible to use a multi-mode fiber. As an example, a small-diameter fiber cable having a diameter of φ0.3 mm to φ0.5 mm that includes a core with a diameter of 105 μm, a cladding with a diameter of 125 μm, and a protective layer serving as an outer skin can be used as the light guide 24.

An illumination optical system 30a and an imaging optical system 30b are provided in the distal end portion 12d of the endoscope 12. The illumination optical system 30a has an illumination lens 32. Through the illumination lens 32, the observation target is illuminated with illumination light propagated through the light guide 24. The imaging optical system 30b includes an objective lens 34, a zoom lens 36, and an imaging sensor 38. Various kinds of light, such as reflected light, scattered light, and fluorescence from the observation target, are incident on the imaging sensor 38 through the objective lens 34 and the zoom lens 36. As a result, an image of the observation target is formed on the imaging sensor 38. The zoom lens 36 is moved freely between the telephoto end and the wide end by operating the zoom operation unit 13d, thereby enlarging or reducing the observation target formed on the imaging sensor 38.

The imaging sensor 38 is a color imaging sensor for imaging the observation target irradiated with illumination light. One of a red (R) color filter, a green (G) color filter, and a blue (B) color filter is provided in each pixel of the imaging sensor 38. The imaging sensor 38 receives violet light to blue light in a B pixel in which a B color filter is provided, receives green light in a G pixel in which a G color filter is provided, and receives red light in an R pixel in which an R color filter is provided. Then, the image signal of each color of RGB is output from the pixel of each color. The imaging sensor 38 transmits the output image signal to a correlated double sampling (CDS)/automatic gain control (AGC) circuit 40.

As the imaging sensor 38, it is possible to use a charge coupled device (CCD) imaging sensor, a complementary metal oxide semiconductor (CMOS) imaging sensor, and the like. Instead of the imaging sensor 38 in which color filters of primary colors of RGB are provided, a complementary color imaging sensor including complementary color filters of cyan (C), magenta (M), yellow (Y), and green (G) may be used. The complementary color imaging sensor outputs image signals of four colors of CMYG. Therefore, by converting the image signals of four colors of CMYG into image signals of three colors of RGB by complementary color-primary color conversion, it is possible to obtain the same RGB image signals as in the imaging sensor 38. Instead of the imaging sensor 38, a monochrome sensor in which no color filter is provided may be used.

The CDS/AGC circuit 40 performs correlated double sampling (CDS) and automatic gain control (AGC) for the analog image signals received from the imaging sensor 38. An analog/digital (A/D) conversion circuit 42 converts the analog image signal having passed through the CDS/AGC circuit 40 into a digital image signal. The A/D conversion circuit 42 inputs the A/D-converted digital image signal to the processor device 16.

The processor device 16 includes an image signal acquisition unit 50, a digital signal processor (DSP) 52, a noise reduction unit 54, a memory 56, a signal processing unit 58, an image processing unit 60, and a video signal generation unit 62.

The image signal acquisition unit 50 acquires a digital image signal from the endoscope 12. The DSP 52 performs various kinds of signal processing, such as defect correction processing, offset processing, gain correction processing, linear matrix processing, gamma conversion processing, and demosaic processing, on the image signal acquired by the image signal acquisition unit 50. The defect correction processing is for correcting the signal of a defective pixel of the imaging sensor 38. The offset processing is for setting an accurate zero level by removing a dark current component from the image signal subjected to the defect correction processing. The gain correction processing is for adjusting the signal level by multiplying the image signal subjected to the offset processing by a specific gain.

The linear matrix processing increases the color reproducibility of the image signal subjected to the gain correction processing. The gamma conversion processing is for adjusting the brightness or saturation of the image signal subjected to the linear matrix processing. By performing demosaic processing (also referred to as isotropic processing or synchronization processing) on the image signal subjected to the gamma conversion processing, the signal of missing color in each pixel is generated by interpolation. Through the demosaic processing, all pixels have signals of RGB colors. The noise reduction unit 54 reduces noise by performing noise reduction processing on the image signal subjected to the demosaic processing or the like by the DSP 52 using, for example, a moving average method or a median filter method. The image signal subjected to the noise reduction processing is stored in the memory 56.

The signal processing unit 58 acquires the image signal subjected to the noise reduction processing from the memory 56. Then, the signal processing unit 58 generates a color endoscope image in which the observation target is reflected (simply, referred to as an image) by performing image processing, for example, color conversion processing, color emphasis processing, and structure emphasis processing, on the acquired image signal. The color conversion processing is a process of performing color conversion on the image signal by 3×3 matrix processing, gradation conversion processing, three-dimensional look-up table (LUT) processing, and the like. The color emphasis processing is performed on the image signal subjected to the color conversion processing. The structure emphasis processing is a process of emphasizing a specific tissue or structure included in an observation target, such as a blood vessel or a pit pattern, and is performed on the image signal after the color emphasis processing.

The content of the color conversion processing, the color emphasis processing, and the structure emphasis processing performed by the signal processing unit 58 differ depending on the observation mode. In the case of the normal mode, the signal processing unit 58 generates an image in which an observation target having a natural color shade is reflected (hereinafter, referred to as a normal observation image), as an endoscope image, by performing the various kinds of signal processing described above. In the case of the special mode, the signal processing unit 58 generates an image emphasizing a structure (hereinafter, referred to as a special observation image), as an endoscope image, by performing the various kinds of signal processing described above for emphasizing at least a structure, such as a blood vessel or a lymphatic vessel included in the observation target. The signal processing unit 58 inputs the generated endoscope image to the image processing unit 60.

In a case where a release operation is performed by the still image acquisition unit 13b, the signal processing unit 58 stores the generated endoscope image in a storage 64. The storage 64 is an external storage device connected to the processor device 16 through a local area network (LAN). The storage 64 is, for example, a file server of a system for filing an endoscope image, such as a picture archiving and communication system (PACS), or a network attached storage (NAS). In the storage 64, in the case of displaying a moving image of the endoscope image on the monitor 18 regardless of the operation of the still image acquisition unit 13b, the moving image of the endoscope image may be stored.

The image processing unit 60 performs processing for emphasizing a structure, such as a blood vessel or a lymphatic vessel, on the image obtained by imaging the observation target with the endoscope. In the present embodiment, a case where a blood vessel is emphasized will be described below. The image processing unit 60 includes an image acquisition unit 70, an extraction unit 72, an index value calculation unit 74, a determination unit 76, a color information setting unit 78, and an image generation unit 80.

The image acquisition unit 70 acquires an image from the signal processing unit 58. In the present embodiment, a case of the special mode will be described below. Therefore, the image acquisition unit 70 acquires a special observation image from the signal processing unit 58.

Specifically, in the special mode, the light source 20 sequentially emits the violet light V and the blue light B. Therefore, as special observation images, the image acquisition unit 70 acquires an image obtained by imaging the observation target illuminated with the violet light V (hereinafter, referred to as an extremely superficial observation image) and an image obtained by imaging the observation target illuminated with the blue light B (hereinafter, referred to as a superficial observation image). In the extremely superficial observation image and the superficial observation image, it is possible to observe not only the mucous membrane of the observation target but also the extremely superficial blood vessel and the superficial blood vessel. In a case where the extremely superficial observation image is compared with the superficial observation image, the contrast of the extremely superficial blood vessel in the extremely superficial observation image is higher than that in the superficial observation image, and the contrast of the superficial blood vessel in the superficial observation image is higher than that in the extremely superficial observation image.

The extraction unit 72 extracts a blood vessel from the image acquired by the image acquisition unit 70, thereby obtaining a blood vessel extraction image. Specifically, the extraction unit 72 obtains a blood vessel extraction image by taking a difference between the extremely superficial observation image and the superficial observation image. More specifically, for example, the extraction unit 72 logarithmically transforms the signal of the extremely superficial observation image and the signal of the superficial observation image, and obtains a blood vessel extraction image based on a signal obtained by subtracting the signal of the extremely superficial observation image from the signal of the superficial observation image. In the blood vessel extraction image, the pixel value of a pixel showing the superficial blood vessel is smaller than the pixel value of a pixel showing the mucous membrane. In the blood vessel extraction image, the pixel value of a pixel showing the extremely superficial blood vessel is larger than the pixel value of a pixel showing the mucous membrane. That is, in the blood vessel extraction image, the superficial blood vessel is displayed darker than the mucous membrane, and the extremely superficial blood vessel is displayed brighter than the mucous membrane. Therefore, the difference between the extremely superficial blood vessel and the superficial blood vessel in the blood vessel extraction image is more noticeable than that in the extremely superficial observation image and the superficial observation image. The extraction unit 72 transmits the blood vessel extraction image to the index value calculation unit 74 and the image generation unit 80.

The index value calculation unit 74 calculates an index value of a blood vessel (hereinafter, referred to as a blood vessel index value) based on the blood vessel extracted by the extraction unit 72. Examples of the blood vessel index value include the number of blood vessels, the number of branches of a blood vessel, the branching angle of a blood vessel, a distance between branch points, the number of crossings between blood vessels, the thickness of a blood vessel, a change in the thickness of a blood vessel, the complexity of a change in the thickness of a blood vessel, the length of a blood vessel, an interval between blood vessels, the depth of a blood vessel, a blood vessel height difference, the inclination of a blood vessel, the area of a blood vessel, the density of blood vessels, the contrast of a blood vessel, the color of a blood vessel, a change in the color of a blood vessel, the degree of meandering of a blood vessel, the blood concentration of a blood vessel, the oxygen saturation of a blood vessel, the proportion of arteries, the proportion of veins, the concentration of administered coloring agent, the running pattern of a blood vessel, and the blood flow rate of a blood vessel. The index value calculation unit 74 calculates at least the two or more blood vessel index values described above. The type of the blood vessel index value calculated by the index value calculation unit 74 is set based on the input operation of the console 19. The type of the blood vessel index value is not limited to the above examples.

The number of blood vessels is the number of blood vessels extracted in the entire endoscope image or in a region of interest. The number of blood vessels is calculated using, for example, the number of branch points (the number of branches) of the extracted blood vessel, the number of intersections (the number of crossings) with other blood vessels, and the like. The number of branches of a blood vessel or the number of crossings between blood vessels is calculated by analyzing the pattern of the blood vessel. The branching angle of a blood vessel is an angle formed by two blood vessels at a branch point. The distance between branch points is a linear distance between an arbitrary branch point and a branch point adjacent thereto or a length along a blood vessel from an arbitrary branch point to a branch point adjacent thereto.

The number of crossings between blood vessels is the number of intersections at which blood vessels having different submucosal depths cross each other on the endoscope image. More specifically, the number of crossings between blood vessels is the number of blood vessels, which are located at relatively shallow submucosal positions, crossing blood vessels located at deep positions.

The thickness of a blood vessel (blood vessel diameter) is a distance between the blood vessel and the boundary of the mucous membrane. For example, the thickness of a blood vessel (blood vessel diameter) is obtained by counting the number of pixels along the lateral direction of the blood vessel from the edge of the extracted blood vessel through the blood vessel. Therefore, the thickness of a blood vessel is the number of pixels. However, in a case where the imaging distance, zoom magnification and the like at the time of capturing an endoscope image are known, the number of pixels can be converted into a unit of length, such as "µm", as necessary.

The change in the thickness of a blood vessel is a blood vessel index value relevant to a variation in the thickness of the blood vessel, and is also referred to as the aperture inconsistency. The change in the thickness of a blood vessel is, for example, a change rate of the blood vessel diameter (also referred to as the degree of expansion). Using the thickness (minimum diameter) of the thinnest portion of the blood vessel and the thickness (maximum diameter) of the thickest portion of the blood vessel, the change rate of the blood vessel diameter is calculated as "blood vessel diameter change rate (%)=minimum diameter/maximum diameter×100".

In a case where an endoscope image obtained by imaging the observation target in a past examination and an endoscope image obtained by imaging the same observation target in a subsequent new examination are used, a temporal change in the thickness of the same blood vessel extracted from the endoscope image obtained by the subsequent new examination with respect to the thickness of the blood vessel extracted from the endoscope image obtained by the past examination may be the change in the thickness of the blood vessel.

As a change in the thickness of the blood vessel, a proportion of a small diameter portion or a proportion of a large diameter portion may be calculated. The small diameter portion is a portion whose thickness is equal to or less than a threshold value. The large diameter portion is a portion whose thickness is larger than the threshold value. The proportion of a small diameter portion is calculated as "proportion of small diameter portion (%)=length of small diameter portion/length of blood vessel×100". Similarly, the proportion of a large diameter portion is calculated as "proportion of large diameter portion (%)=length of large diameter portion/length of blood vessel×100".

The complexity of the change in the thickness of a blood vessel (hereinafter, referred to as the "complexity of the thickness change") is a blood vessel index value indicating how complex the change is in a case where the thickness of the blood vessel changes, and is a blood vessel index value calculated by combining a plurality of blood vessel index values indicating the change in the thickness of the blood vessel (that is, the change rate of the blood vessel diameter, the proportion of the small diameter portion, or the proportion of the large diameter portion). The complexity of the thickness change can be calculated, for example, by the product of the change rate of the blood vessel diameter and the proportion of the small diameter portion.

The length of the blood vessel is the number of pixels obtained by counting the extracted blood vessel along the longitudinal direction.

The interval between blood vessels is the number of pixels showing the mucous membrane between the edges of the extracted blood vessel. In the case of one extracted blood vessel, the interval between blood vessels has no value.

The depth of a blood vessel is measured with the mucous membrane (more specifically, the mucosal surface) as a reference. The depth of a blood vessel with the mucous membrane as a reference can be calculated based on, for example, the color of the blood vessel. In the case of the special observation image, for example, a superficial blood vessel located near the mucosal surface (located at a shallow submucosal position) is expressed by a magenta type color, and a middle deep layer blood vessel located far from the mucosal surface (located at a deep submucosal position) is expressed by a cyan type color. Therefore, the index value calculation unit 74 calculates the depth of the blood vessel with the mucous membrane as a reference for each pixel based on the balance of the signals of the respective colors of R, G, and B of the pixels extracted as a blood vessel.

The height difference of a blood vessel is the magnitude of the difference in the depth of the blood vessel. For example, the height difference of one blood vessel of interest is calculated by the difference between the depth (maximum depth) of the deepest portion of the blood vessel and the depth (minimum depth) of the shallowest portion. In a case where the depth is constant, the height difference is zero.

The inclination of a blood vessel is the change rate of the depth of the blood vessel, and is calculated using the length of the blood vessel and the depth of the blood vessel. That is, the inclination of a blood vessel is calculated as "inclination of blood vessel=depth of blood vessel/length of blood vessel". The blood vessel may be divided into a plurality of sections, and the inclination of the blood vessel may be calculated in each section.

The area of a blood vessel is the number of pixels extracted as a blood vessel or a value proportional to the number of pixels extracted as a blood vessel. The area of a blood vessel is calculated within the region of interest, outside the region of interest, or for the entire endoscope image.

The density of blood vessels is a proportion of blood vessels in a unit area. A region of a specific size (for example, a region of a unit area) including pixels for calculating the density of blood vessels at its approximate center is cut out, and the proportion (area) of blood vessels occupying all the pixels within the region is calculated. By performing this on all the pixels of the region of interest or the entire endoscope image, the density of blood vessels of each pixel can be calculated.

The contrast of a blood vessel is the relative contrast of the blood vessel with respect to the mucous membrane of the observation target. The contrast of a blood vessel is calculated as, for example, "$Y_V/Y_M$" or "$(Y_V-Y_M)/(Y_V+Y_M)$", using the brightness $Y_V$ of the blood vessel and the brightness $Y_M$ of the mucous membrane.

The color of a blood vessel is each value of RGB of pixels showing the blood vessel. The change in the color of a blood vessel is a difference or ratio between the maximum value and the minimum value of the RGB values of pixels showing the blood vessel. For example, the ratio between the maximum value and the minimum value of the B value of a pixel showing the blood vessel, the ratio between the maximum value and the minimum value of the G value of a pixel showing the blood vessel, or the ratio between the maximum value and the minimum value of the R value of a pixel showing the blood vessel indicates a change in the color of the blood vessel. Needless to say, conversion into complementary colors may be performed to calculate the color of the blood vessel and a change in the color of the blood vessel for each value of cyan, magenta, yellow, green, and the like.

The degree of meandering of a blood vessel is a blood vessel index value indicating the size of a range in which the blood vessel travels while meandering. The degree of meandering of a blood vessel is, for example, the area (the number of pixels) of a minimum rectangle including the blood vessel for which the degree of meandering is to be calculated. The ratio of the length of the blood vessel to the linear distance between the start point and the end point of the blood vessel may be used as the degree of meandering of the blood vessel.

The blood concentration of a blood vessel is a blood vessel index value proportional to the amount of hemoglobin contained in a blood vessel. Since the ratio (G/R) of the G value to the R value of a pixel showing a blood vessel is proportional to the amount of hemoglobin, the blood concentration can be calculated for each pixel by calculating the value of G/R.

The oxygen saturation of a blood vessel is the amount of oxygenated hemoglobin to the total amount of hemoglobin (total amount of oxygenated hemoglobin and reduced hemoglobin). The oxygen saturation can be calculated by using an endoscope image obtained at the time of illuminating the observation target with light in a specific wavelength range (for example, blue light having a wavelength of about 470±10 nm) having a large difference between the light absorption coefficients of oxygenated hemoglobin and reduced hemoglobin. In a case where blue light having a wavelength of about 470±10 nm is used, the B value of the pixel showing the blood vessel is correlated with the oxygen saturation. Therefore, by using a table or the like that associates the B value with the oxygen saturation, it is possible to calculate the oxygen saturation of each pixel showing the blood vessel.

The proportion of arteries is the ratio of the number of pixels of arteries to the number of pixels of all the blood vessels. Similarly, the proportion of veins is the ratio of the number of pixels of veins to the number of pixels of all the blood vessels. Arteries and veins can be distinguished by oxygen saturation. For example, assuming that a blood vessel having an oxygen saturation of 70% or more is an artery and a blood vessel having an oxygen saturation less than 70% is a vein, extracted blood vessels can be distinguished into arteries and veins. Therefore, the proportion of arteries and the proportion of veins can be calculated.

The concentration of an administered coloring agent is the concentration of a coloring agent sprayed on the observation target or the concentration of a coloring agent injected into the blood vessel by intravenous injection. The concentration of the administered coloring agent is calculated, for example, by the ratio of the pixel value of the coloring agent color to the pixel value of a pixel other than the coloring agent color. For example, in a case where a coloring agent for coloring in blue is administered, B/G, B/R, and the like indicate the concentration of the coloring agent fixed (or temporarily adhered) to the observation target.

The traveling pattern of a blood vessel is a blood vessel index value relevant to the traveling direction of a blood vessel. The traveling pattern of a blood vessel is, for example, an average angle (traveling direction) of a blood vessel with respect to a reference line arbitrarily set, a dispersion (variation in traveling direction) of an angle formed by a blood vessel with respect to a reference line set arbitrarily, and the like.

The blood flow rate (also referred to as a blood flow speed) of a blood vessel is the number of red blood cells that can pass per unit time. In a case where an ultrasound probe is used together through the forceps channel of the endoscope 12 or the like, the blood flow rate of the blood vessel can be calculated by calculating the Doppler shift frequency of each pixel showing the blood vessel of the endoscope image using the signal obtained by the ultrasound probe.

The index value calculation unit 74 calculates a blood vessel index value for each pixel of the endoscope image. For example, the blood vessel index value of one pixel is calculated using the data of pixels in a predetermined range including a pixel whose blood vessel index value is to be calculated (for example, a range of 99×99 pixels centered on the pixel whose blood vessel index value is to be calculated). For example, in the case of calculating the thickness of a blood vessel as a blood vessel index value, the "thickness of a blood vessel" for each pixel is a statistic of the thickness of a blood vessel in the predetermined range. The statistic is a so-called basic statistic, and is, for example, a maximum value, a minimum value, an average value, a median, or a mode. Statistics other than the exemplified values may also be used. For example, a value (ratio between the maximum value and the minimum value or the like) calculated using a so-called representative value, such as the maximum value, the minimum value, the average value, the median, or the mode, or a so-called scattering degree, such as a dispersion, a standard deviation, and a variation coefficient, can be used.

In a case where a region of interest is set in a part of the endoscope image by the operation of the console 19, the index value calculation unit 74 calculates a blood vessel index value within the set region of interest. In a case where a region of interest is not set or a case where the entire endoscope image is set as a region of interest, the index value calculation unit 74 calculates a blood vessel index value for the entire endoscope image.

In the case of setting a region of interest, the index value calculation unit 74 calculates a statistic of a blood vessel index value of each pixel included in the region of interest, and sets the value as the blood vessel index value of the region of interest. For example, in the case of calculating the thickness of a blood vessel as a blood vessel index value, the "thickness of a blood vessel" of each pixel is calculated as described above. In a case where a region of interest is set, a statistic of the "thickness of a blood vessel" of each pixel included in the region of interest is further calculated, and one "thickness of a blood vessel" is calculated for one set region of interest. The same is true for a case where the entire endoscope image is set as a region of interest.

The statistic in the case of calculating a blood vessel index value for each pixel and the statistic in the case of calculating a blood vessel index value of a region of interest may be the same statistic, or may be different. For example, in the case of calculating the thickness of a blood vessel for each pixel, an average value of the thickness of the blood vessel appearing in a "predetermined range" may be calculated. Thereafter, even in the case of calculating the thickness of a blood vessel in the region of interest, the average value of the thickness of the blood vessel of each pixel may be calculated, or a mode of the thickness of the blood vessel of each pixel may be calculated.

Depending on the type of the blood vessel index value to be calculated, a relationship between the method of calculating the statistic in the case of calculating the blood vessel index value for each pixel and the method of calculating the statistic in the case of calculating the blood vessel index value of the region of interest, and the like, it is possible to omit the blood vessel index value for each pixel. For example, in the case of the "thickness of a blood vessel", an average value of the thickness of the blood vessel appearing in the region of interest can be set as the thickness of the blood vessel in the region of interest.

The determination unit 76 determines whether each of the plurality of blood vessel index values calculated by the index value calculation unit 74 is a normal value indicating a normal state or an abnormal value different from the normal state. Specifically, the determination unit 76 performs the determination by comparing the blood vessel index value calculated by the index value calculation unit 74 with a specific threshold value. Then, the determination unit 76 sets the blood vessel index value determined to be an abnormal value as an abnormal index value, and sets the blood vessel index value determined to be a normal value as a normal index value.

For example, it is known that the density of blood vessels in a part where there is a possibility of lesion, such as cancer, is higher than that of a part in a normal state. Therefore, the determination unit 76 performs determination as an abnormal value in a case where the density of blood vessels is higher than the threshold value, and performs determination as a normal value in a case where the density of blood vessels is equal to or less than the threshold value.

It is known that, in a part where there is a possibility of lesion, one blood vessel branches into a plurality of blood vessels and the shape of the blood vessel becomes complicated. Therefore, the determination unit 76 performs determination as an abnormal value in a case where the number of branches of the blood vessel is larger than the threshold value, and performs determination as a normal value in a case where the number of branches of the blood vessel is equal to or less than the threshold value.

It is known that the oxygen saturation of the blood vessel in a part where there is a possibility of a lesion is lower than that of a part in a normal state. Therefore, the determination unit 76 performs determination as an abnormal value in a case where the n oxygen saturation is lower than the threshold value, and performs determination as a normal value in a case where the oxygen saturation is equal to or higher than the threshold value.

In the case of generating an emphasized image in which a difference in the depth of a blood vessel is emphasized (which will be described in detail later), the determination unit 76 may omit the determination regarding the depth of the blood vessel. For example, in a case where the abnormal index value enables determination regarding at which depth the blood vessel is located by emphasizing the difference in the depth of the blood vessel, the determination unit 76 may omit the determination regarding the depth of the blood vessel.

The color information setting unit 78 sets color information for the abnormal index value or the normal index value. In the present embodiment, a case of setting color information for the abnormal index value will be described below. Specifically, the color information setting unit 78 sets color information based on the position of the abnormal index value on a plane formed by the Cb axis and the Cr axis in a YCbCr space, for example. More specifically, in a case where the determination unit 76 determines that there is only one abnormal index value, the color information setting unit 78 associates the abnormal index value with the Cb axis or the Cr axis. For example, the color information setting unit 78 reduces the Cb value or the Cr value in a case where the abnormal index value is small, and increases the Cb value or the Cr value in a case where the abnormal index value is large. Accordingly, the color information setting unit 78 sets the color information according to the position of the abnormal index value on the Cr axis or the Cb axis. In a case where the abnormal index value enables determination regarding at which depth the blood vessel is located, the color information setting unit 78 associates the depth of the blood vessel with one axis, and associates the blood vessel index value (abnormal index value) different from the depth of the blood vessel with the other axis.

In a case where there are two abnormal index values, the color information setting unit 78 may set the color information for each abnormal index value according to the position of each abnormal index value on the Cr axis or the Cb axis by associating one abnormal index value with the Cr axis and associating the other abnormal index value with the Cb axis. In a case where there are three abnormal index values, the color information may be set for each abnormal index value by changing the hue for each abnormal index value on the plane formed by the Cb axis and the Cr axis.

In a case where there is no abnormal index value, the color information setting unit 78 may set color information for one of the blood vessel index values described above, or may not set color information. In the case of setting color information in a case where there is no abnormal index value, the color information setting unit 78 sets the color information for the depth of the blood vessel, for example.

Based on the color information set by the color information setting unit 78, the image generation unit 80 generates an emphasized image in which the blood vessel is emphasized. Specifically, the image generation unit 80 generates an emphasized image having a plurality of output channels using the extremely superficial observation image or the superficial observation image and the blood vessel extraction image. More specifically, the image generation unit 80 assigns the extremely superficial observation image or the superficial observation image to a brightness channel Y, and assigns the blood vessel extraction image to two color difference channels Cb and Cr. In the case of assigning the blood vessel extraction image to the color difference channels Cb and Cr, multiplication of a specific coefficient may be performed. Then, according to the inverse transformation of ITU-R. 601, the emphasized image of RGB is generated from the brightness channel Y and the color difference channels Cb and Cr. In the emphasized image, a region of the abnormal index value is emphasized by coloring the pixels of the abnormal index value based on the color information.

In a case where the abnormal index value enables determination regarding at which depth the blood vessel is located, an emphasized image in which the region of the abnormal index value is emphasized for each depth may be generated by coloring according to the abnormal index value and the depth of the blood vessel. In a case where there is no abnormal index value (that is, in a case where all the blood vessel index values are normal values), the image generation unit 80 may generate an emphasized image in which the difference in the depth of the blood vessel is emphasized by coloring according to the depth of the blood vessel. In a case where there is no abnormal index value and color information is not set by the color information setting unit 78, an image may be generated without performing the coloring as described above.

The video signal generation unit 62 converts the endoscope image subjected to the image processing of the image processing unit 60 into a video signal that can be output and displayed on the monitor 18. The monitor 18 displays a normal observation image in the case of the normal mode, and displays an emphasized image (special observation image) in the case of the special mode.

In the present embodiment, a case where the index value calculation unit 74 calculates three kinds of blood vessel index values of the density of blood vessels, the number of branches of the blood vessel, and the depth of the blood vessel using the blood vessel extraction image obtained by the extraction unit 72 will be described below.

Figure 3:
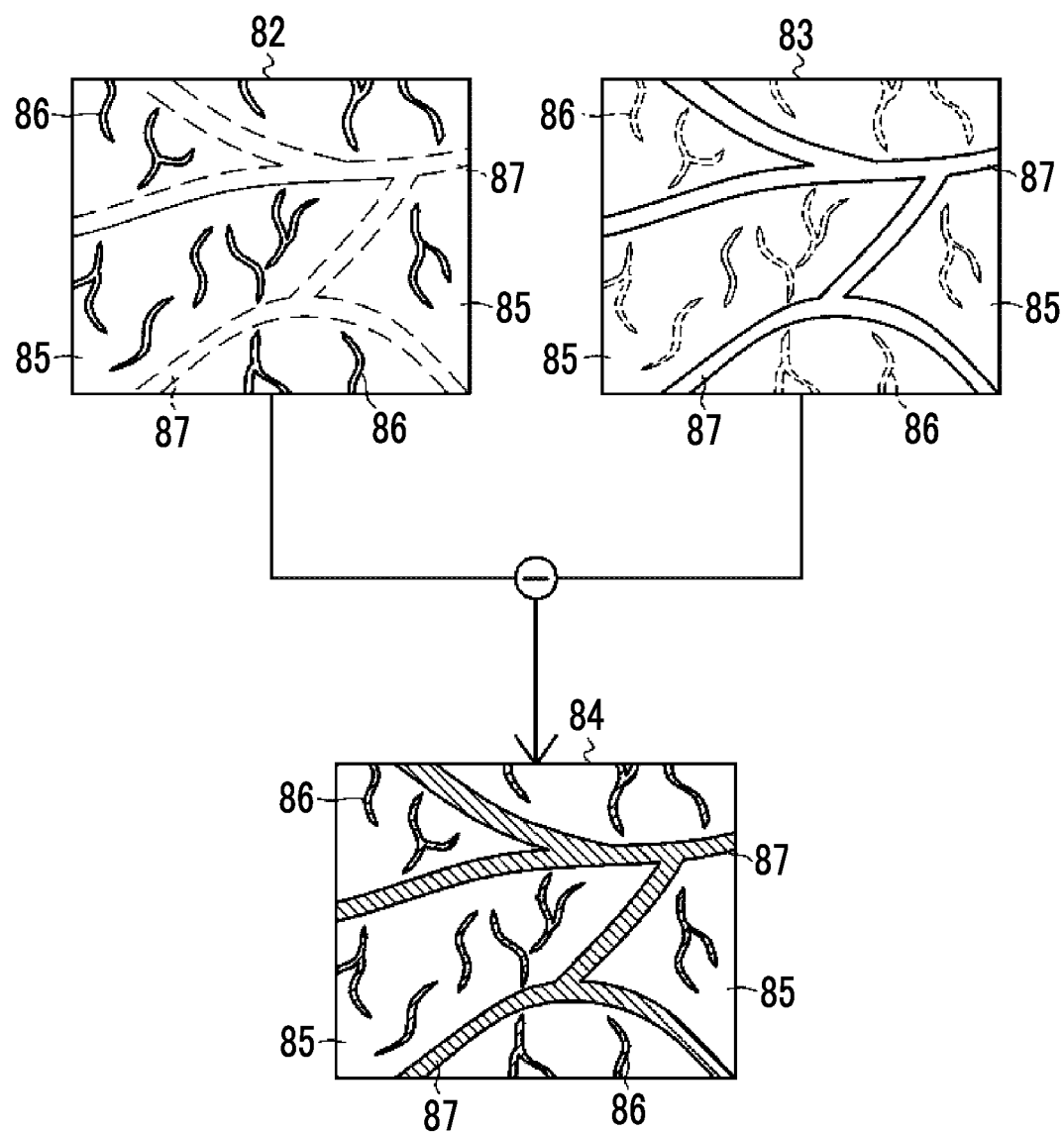
FIG. 3 is an explanatory diagram illustrating the extraction of a blood vessel.

As shown in FIG. 3, the extraction unit 72 extracts blood vessels by taking a difference between an extremely superficial observation image 82 and a superficial observation image 83, thereby obtaining a blood vessel extraction image 84. In the extremely superficial observation image 82 and the superficial observation image 83, it is possible to observe a mucous membrane 85 of the observation target, an extremely superficial blood vessel 86 located at a shallow submucosal position, and a superficial blood vessel 87 located at a deeper submucosal position than the extremely superficial blood vessel 86. In a case where the extremely superficial observation image 82 is compared with the superficial observation image 83, the contrast of the extremely superficial blood vessel 86 in the extremely superficial observation image 82 is higher than that in the superficial observation image 83, and the contrast of the superficial blood vessel 87 in the superficial observation image 83 is higher than that in the extremely superficial observation image 82. The difference between the extremely superficial blood vessel 86 and the superficial blood vessel 87 in the blood vessel extraction image 84 is more noticeable than that in the extremely superficial observation image 82 and the superficial observation image 83.

Figure 4:
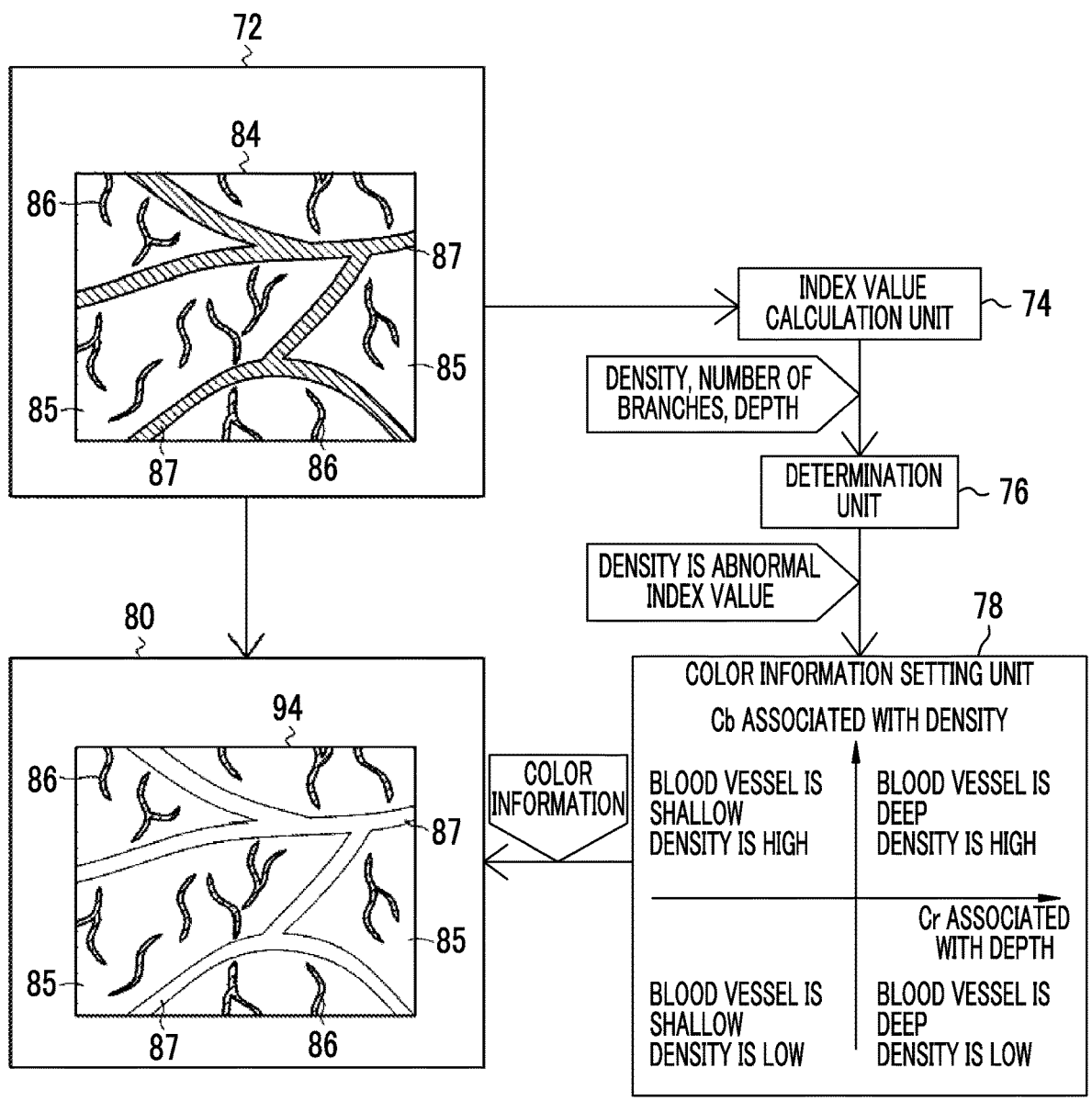
FIG. 4 is an explanatory diagram illustrating the generation of an emphasized image.

As shown in FIG. 4, the index value calculation unit 74 calculates three kinds of blood vessel index values of the density, the number of branches, and the depth of the extremely superficial blood vessel 86 using the blood vessel extraction image 84 obtained from the extraction unit 72. In this example, a case will be described in which the abnormal index value enables determination regarding at which depth the blood vessel is located. Therefore, the determination unit 76 performs determination regarding the density and the number of branches, but determination regarding the depth may be omitted. Specifically, the determination unit 76 performs determination as an abnormal value in a case where the density of the extremely superficial blood vessel 86 is higher than the threshold value, and performs determination as a normal value in a case where the density of the extremely superficial blood vessel 86 is equal to or less than the threshold value. Similarly, the determination unit 76 performs determination as an abnormal value in a case where the number of branches of the extremely superficial blood vessel 86 is larger than the threshold value, and performs determination as a normal value in a case where the number of branches of the extremely superficial blood vessel 86 is equal to or less than the threshold value. The determination unit 76 determines, for example, the density of the extremely superficial blood vessel 86 to be an abnormal value.

In the YCbCr space, the color information setting unit 78 associates the density with the Cb axis, and associates the depth with the Cr axis. The color information setting unit 78 increases the Cb value in a case where the density of blood vessels is high, and reduces the Cb value in a case where the density of blood vessels is low. The color information setting unit 78 increases the Cr value in a case where the blood vessel is deep, and reduces the Cr value in a case where the blood vessel is shallow. In this manner, the color information setting unit 78 sets color information (for example, red type color or the like) based on the position of the density on the Cb axis and the position of the depth on the Cr axis.

Using the blood vessel extraction image 84, the image generation unit 80 generates an emphasized image 94 based on the color information. Specifically, the image generation unit 80 assigns the extremely superficial observation image 82 to the brightness channel Y, and assigns the blood vessel extraction image 84 to the color difference channels Cb and Cr. By assigning the extremely superficial observation image 82 to the brightness channel Y, the extremely superficial observation image 82 is used as brightness information. As a result, the extremely superficial blood vessel 86 is emphasized more than the superficial blood vessel 87. In the emphasized image 94, pixels at which the density of the extremely superficial blood vessel 86 is an abnormal value are colored with a specific color (for example, red type color or the like) based on the color information, so that a region where the density of the extremely superficial blood vessel 86 is an abnormal value is emphasized.

Figure 5:
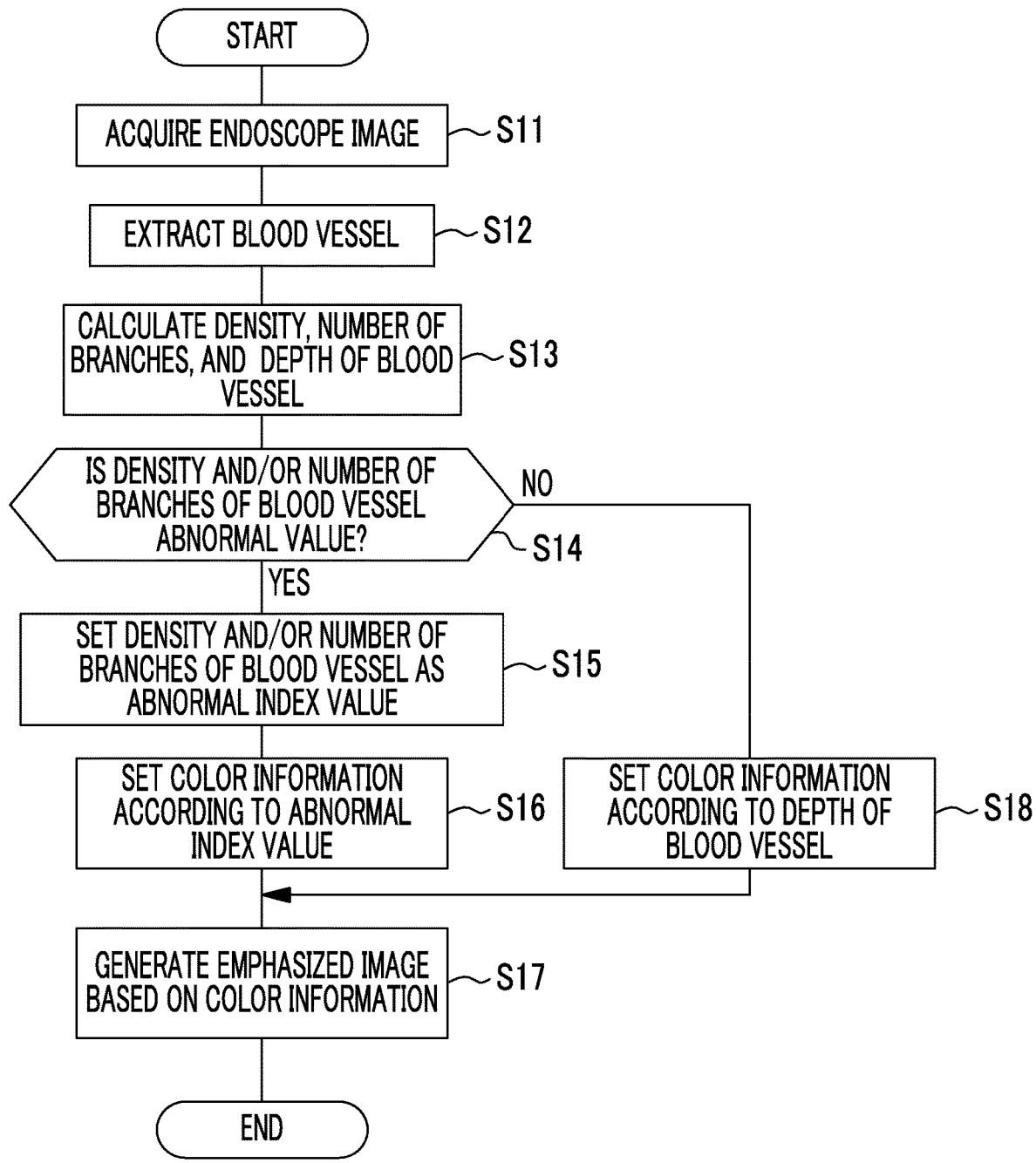
FIG. 5 is a flowchart showing the operation of the endoscope system of the first embodiment.

Next, the operation of the endoscope system 10 in a special mode will be described according to the flowchart of FIG. 5.

The image acquisition unit 70 acquires a special observation image (endoscope image) obtained by imaging the observation target with the endoscope 12 (S11). Specifically, in the special mode, the violet light V and the blue light B are sequentially emitted. Therefore, the image acquisition unit 70 acquires the extremely superficial observation image 82 obtained by imaging the observation target illuminated with the violet light V and the superficial observation image 83 obtained by imaging the observation target illuminated with the blue light B.

The extraction unit 72 extracts blood vessels by taking a difference between the extremely superficial observation image 82 and the superficial observation image 83 acquired by the image acquisition unit 70 (S12), thereby obtaining the blood vessel extraction image 84. The difference between the extremely superficial blood vessel 86 and the superficial blood vessel 87 in the blood vessel extraction image 84 is more noticeable than that in the extremely superficial observation image 82 and the superficial observation image 83. After the blood vessels are extracted by the extraction unit 72, the index value calculation unit 74 calculates three kinds of blood vessel index values of the density, the number of branches, and the depth of the extremely superficial blood vessel 86 using the blood vessel extraction image 84 (S13).

The determination unit 76 determines whether or not the density of the extremely superficial blood vessel 86 is an abnormal value (S14). In a case where the density of the extremely superficial blood vessel 86 is determined to be an abnormal value, the determination unit 76 sets the density of the extremely superficial blood vessel 86 as an abnormal index value (S15). Similarly, the determination unit 76 determines whether or not the number of branches of the extremely superficial blood vessel 86 is an abnormal value (S14), and sets the number of branches of the extremely superficial blood vessel 86 as an abnormal index value in a case where the number of branches of the extremely superficial blood vessel 86 is determined to be an abnormal value (S15). For example, as described above, only the density of the extremely superficial blood vessel 86 is determined to be an abnormal value.

The color information setting unit 78 sets color information for the density that is an abnormal index value (S16). In this example, as described above, since the abnormal index value enables determination regarding at which depth the blood vessel is located, the color information setting unit 78 sets the color information by associating the density with the Cb axis and associating the depth with the Cr axis in the YCbCr space. The image generation unit 80 generates the emphasized image 94 based on the color information set by the determination unit 76 (S17). In the emphasized image 94, pixels having abnormal density values are emphasized by coloring using a specific color (for example, red type color) based on the color information. The emphasized image 94 generated by the image generation unit 80 is displayed on the monitor 18. As a result of the determination of the determination unit 76, in a case where there is no abnormal index value (NO in S14), the color information setting unit 78 sets color information for, for example, the depth of the blood vessel (S18), and the image generation unit 80 generates an emphasized image in which the difference in the depth of the blood vessel is emphasized based on the color information (S17).

As described above, since a plurality of blood vessel index values are calculated, it is determined whether each blood vessel index value is a normal value or an abnormal value, and an emphasized image is generated based on color information corresponding to an abnormal index value that is a blood vessel index value determined to be an abnormal value, the color is displayed by narrowing down the range to blood vessel index values that are to be noticed even in a case where a plurality of blood vessel index values are used. Therefore, it is possible to assist the doctor to quickly perform determination upon diagnosis.

In the first embodiment described above, the color information setting unit 78 reduces the Cb value or the Cr value in a case where the abnormal index value is small, and increases the Cb value or the Cr value in a case where the abnormal index value is large. However, conversely, the color information setting unit 78 may increase the Cb value or the Cr value in a case where the abnormal index value is small and reduce the Cb value or the Cr value in a case where the abnormal index value is large. Such setting may be performed based on the input operation of the console 19 or the like.

In the first embodiment described above, the abnormal index value is associated with the Cb axis. However, the abnormal index value may be associated with the Cr axis, or may be associated with both the Cb axis and the Cr axis. An axis with which the abnormal index value is to be associated may be set based on the input operation of the console 19. Color information may be set by changing the abnormal index value in the hue direction or the saturation direction.

The color information setting unit 78 may associate the abnormal index value not only with the Cb axis and the Cr axis but also the Y axis.

Although the color information setting unit 78 sets the color information using the YCbCr space, various color spaces, such as Lab, Luv, RGB, and HLS, may be used in addition to the YCbCr space. In a case where such various color spaces are used, it is preferable that the abnormal index value is preferentially associated with the axis indicating the hue.

In the first embodiment described above, the type of the blood vessel index value calculated by the index value calculation unit 74 is selected based on the input operation of the console 19. However, the type of the blood vessel index value calculated by the index value calculation unit 74 may be determined in advance. Alternatively, the index value calculation unit 74 may calculate all types of blood vessel index values.

On the monitor 18, the type of the abnormal index value may be displayed together with the emphasized image 94.

Second Embodiment

Figure 6:
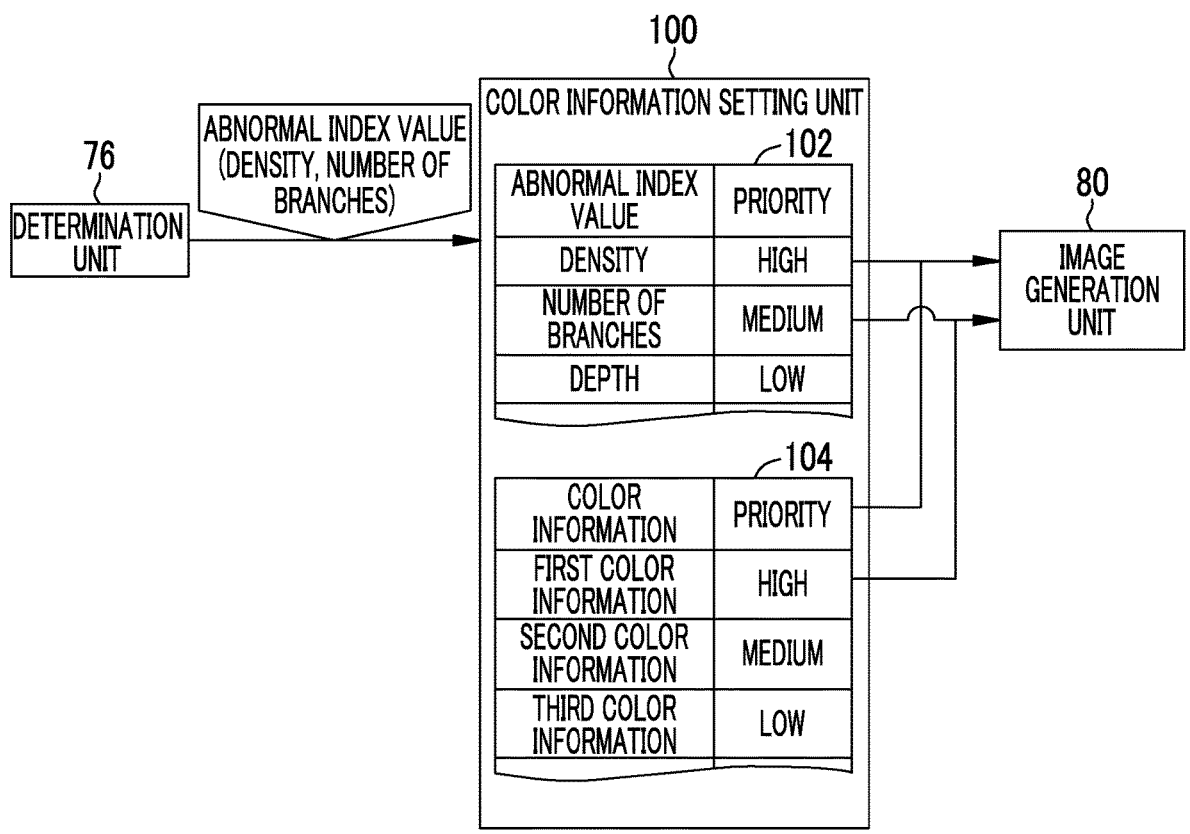
FIG. 6 is a block diagram showing a function of a color information setting unit of a second embodiment.

In the first embodiment described above, the color information setting unit 78 sets the color information for one abnormal index value. In a second embodiment, however, for a plurality of abnormal index values, the color information setting unit 78 may set the color information for each abnormal index value. In this case, instead of the color information setting unit 78 of the first embodiment described above, a color information setting unit 100 shown in FIG. 6 is provided. Hereinafter, the same members as in the first embodiment are denoted by the same reference numerals, and the explanation thereof will be omitted.

As shown in FIG. 6, the color information setting unit 100 has an abnormal index value priority table 102 and a color information priority table 104. In the abnormal index value priority table 102, the types of a plurality of abnormal index values are stored with their priorities determined for each abnormal index value. The types of abnormal index values stored in the abnormal index value priority table 102 are set based on the input operation of the console 19 among all the above types of blood vessel index values. For example, in the abnormal index value priority table 102, "density", "the number of branches", and "depth" are stored as abnormal index values. Priorities are set based on the input operation of the console 19. For example, in a case where "high", "medium", and "low" are expressed in descending order of priority, the priority of the density is set to "high", the priority of the number of branches is set to "medium", and the priority of the depth is set to "low".

In the color information priority table 104, the types of a plurality of pieces of color information are stored with their priorities determined for each piece of color information. A plurality of pieces of color information have at least different hues. For example, there are first color information of red type color, second color information of cyan type color, and third color information of green type color. Such color information is set based on the input operation of the console 19. A plurality of pieces of color information may have different saturations.

A priority is set for each of the pieces of first to third color information. Priorities are set based on the input operation of the console 19. For example, in a case where "high", "medium", and "low" are expressed in descending order of priority, the priority of the first color information is set to "high", the priority of the second color information is set to "medium", and the priority of the third color information is set to "low". The higher the visibility of the color information in the emphasized image, the higher the priority may be set.

Then, the color information setting unit 100 assigns the abnormal index value stored in the abnormal index value priority table 102 and the color information stored in the color information priority table 104. Specifically, the color information setting unit 100 preferentially assigns color information having a higher priority to an abnormal index value having a higher priority. For example, in a case where the density and the number of branches of the extremely superficial blood vessel 86 are determined to be abnormal index values by the determination unit 76, the color information setting unit 100 assigns the first color information whose priority is "high" to the density of the extremely superficial blood vessel 86 whose priority is "high". Then, the color information setting unit 100 assigns the second color information whose priority is "medium" to the number of branches of the extremely superficial blood vessel 86 whose priority is "medium".

As described above, in a case where there are a plurality of abnormal index values, by assigning color information having a higher priority to an abnormal index value having a higher priority, the color is displayed by narrowing down the range to more useful blood vessel index values among the blood vessel index values that are to be noticed, it is possible to assist quick diagnosis using a more useful blood vessel index value.

In the second embodiment described above, the abnormal index value corresponding to the blood vessel index value set based on the input operation of the console 19 is stored in the abnormal index value priority table 102. However, all types of abnormal index values corresponding to all types of blood vessel index values or abnormal index values corresponding to any of all types of blood vessel index values may be stored in advance. In this example, priorities are expressed by "high", "medium", and "low". However, priorities may be arbitrarily expressed. For example, priorities may be expressed by numerals, such as "1", "2", and "3".

Third Embodiment

Figure 7:
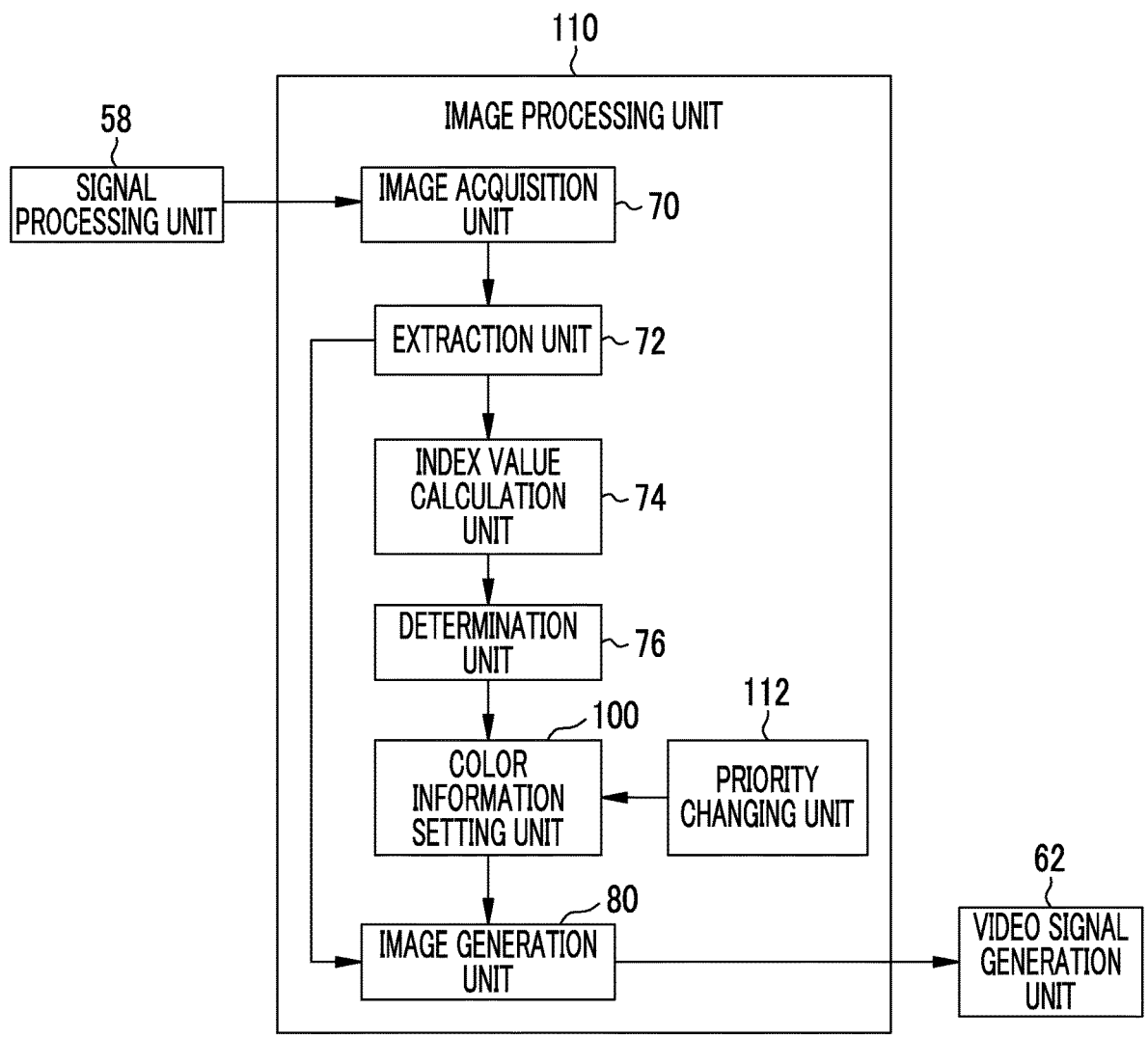
FIG. 7 is a block diagram showing a function of an image processing unit of a third embodiment.

In the second embodiment described above, the color information setting unit 78 sets the color information according to the priority set in advance for the abnormal index value. In a third embodiment, however, the priority of each abnormal index value is changed, and color information is set according to the changed priority. In this case, instead of the image processing unit 60 of the second embodiment described above, an image processing unit 110 shown in FIG. 7 is provided. The image processing unit 110 has a priority changing unit 112 in addition to each component of the image processing unit 60 of the second embodiment described above.

Figure 8:
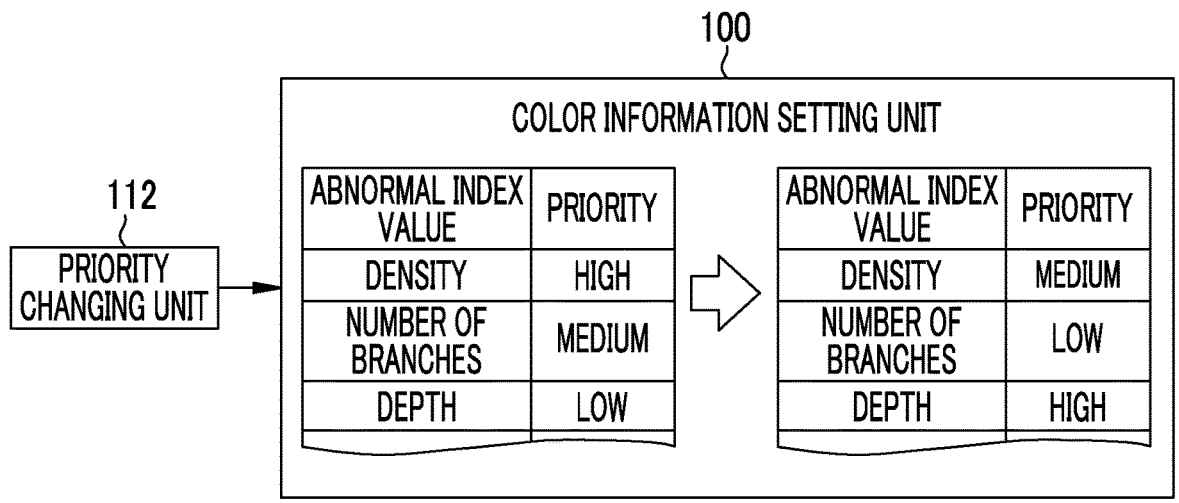
FIG. 8 is a block diagram showing a function of a priority changing unit.

As shown in FIG. 8, the priority changing unit 112 changes the priority of each abnormal index value stored in the abnormal index value priority table 102 of the color information setting unit 100. For example, the priority changing unit 112 changes the priority of the density stored in the abnormal index value priority table 102 from "high" to "medium", changes the priority of the number of branches from "medium" to "low", and changes the priority of the depth from "low" to "high".

The priority changing unit 112 changes the priority based on the observation conditions. As the observation conditions, any of the type of the endoscope 12, the observation distance from the observation target, the zoom magnification of the endoscope 12, the type of observation mode, a coloring agent sprayed on the observation target, and acquisition of different observation distances from one image is selected.

Hereinafter, the function of the priority changing unit 112 will be described for each of the above-described observation conditions according to six embodiments of Embodiments 3A to 3F.

Embodiment 3A

The image processing unit 110 of Embodiment 3A has an endoscope identification unit. The endoscope identification unit identifies the type of the endoscope 12 connected to the processor device 16. Specifically, the endoscope identification unit determines whether the type of the endoscope 12 is an upper observation endoscope used for observing the upper digestive tract or a lower observation endoscope used for observing the lower digestive tract, thereby determining whether or not replacement between the upper observation endoscope and the lower observation endoscope has been performed.

In a case where the replacement between the upper observation endoscope and the lower observation endoscope is performed as the observation conditions, the priority changing unit 112 changes the priority as described above. For example, in a case where the upper observation endoscope is replaced with the lower observation endoscope, the priority changing unit 112 changes the priority of the density stored in the abnormal index value priority table 102 from "high" to "medium", changes the priority of the number of branches from "medium" to "low", and changes the priority of the depth from "low" to "high". In this manner, in a case where the endoscope 12 is replaced, the priority is changed. Therefore, even in a case where the priority of the blood vessel index value that are to be noticed is different between the upper digestive tract and the lower digestive tract, it is possible to display the color by narrowing down the range to blood vessel index values having high priorities after the change.

Embodiment 3B

In Embodiment 3B, the priority changing unit 112 acquires an observation distance from the observation target. The observation distance can be acquired by the exposure amount of the endoscope image acquired by the image acquisition unit 70, frequency analysis of the endoscope image, or the like. In the case of acquiring the observation distance from the exposure amount of the endoscope image, a first observation distance is acquired based on the exposure amount of the endoscope image obtained in a case where a change in the zoom magnification is started, and a second observation distance is acquired based on the exposure amount of the endoscope image obtained in a case where the change in the zoom magnification is ended. In the case of acquiring the observation distance by frequency analysis of the endoscope image, the first observation distance is acquired by performing frequency analysis of an endoscope image obtained in a case where a change in the zoom magnification is started, and the second observation distance is acquired by performing frequency analysis of an endoscope image obtained in a case where the change in the zoom magnification is ended. In this manner, the priority changing unit 112 acquires the first observation distance and the second observation distance different from the first observation distance.

In a case where the first observation distance is changed to the second observation distance as the observation conditions, the priority changing unit 112 changes the priority as described above. Some or all of the blood vessels appearing in the endoscope image obtained in a case where the observation distance is a short distance may not appear in the endoscope image obtained in a case where the observation distance is a long distance. Therefore, a blood vessel index value obtained in the case of a long distance may not be so accurate as a blood vessel index value obtained in the case of a short distance. For example, in the case of a long distance, it is difficult to accurately calculate the number of branches of a blood vessel. However, in the case of a short distance, it is possible to accurately calculate the number of branches of a blood vessel. Therefore, in a case where the second observation distance is longer than the first observation distance, the priority changing unit 112 changes the priority of the number of branches stored in the abnormal index value priority table 102 from "medium" to "low" in a case where the first observation distance is changed to the second observation distance. In this manner, in a case where the observation distance is changed, the priority is changed. Therefore, even in a case where the priority of the blood vessel index value that are to be noticed differs depending on the observation distance, it is possible to display the color by narrowing down the range to blood vessel index values having high priorities after the change.

Embodiment 3C

In Embodiment 3C, the priority changing unit 112 acquires the first zoom magnification and the second zoom magnification different from the first zoom magnification from the zoom operation unit 13d. Then, in a case where the first zoom magnification is changed to the second zoom magnification as the observation conditions, the priority changing unit 112 changes the priority as described above. For example, in a case where the second zoom magnification is lower than the first zoom magnification (that is, a long distance), some or all of the blood vessels appearing in the endoscope image obtained at the first zoom magnification may not appear in the endoscope image obtained at the second zoom magnification in a case where in a case where the first zoom magnification is changed to the second zoom magnification. Therefore, a blood vessel index value obtained at the second zoom magnification may not be so accurate as a blood vessel index value obtained at the first zoom magnification. For example, it is difficult to accurately calculate the number of branches of a blood vessel at the second zoom magnification of a long distance. However, it is possible to accurately calculate the number of branches of a blood vessel at the first zoom magnification of a short distance. Therefore, in a case where the first zoom magnification is changed to the second zoom magnification, the priority changing unit 112 changes the priority of the number of branches stored in the abnormal index value priority table 102 from "medium" to "low". In this manner, in a case where the zoom magnification is changed, the priority is changed. Therefore, even in a case where the priority of the blood vessel index value that are to be noticed differs depending on the zoom magnification, it is possible to display the color by narrowing down the range to blood vessel index values having high priorities after the change.

Embodiment 3D

In Embodiment 3D, the special mode includes a first special mode and a second special mode. The first special mode and the second special mode are modes in which an emphasized image is generated using two or more types of blood vessel index values as in each of the embodiments described above. In the first special mode, all or some of the types of blood vessel index values used for generating an emphasized image are different from those in the second special mode. The type of the blood vessel index value is set for each special mode based on the input operation of the console 19. In the first special mode and the second special mode, the type of the blood vessel index value may be set in advance. The special mode corresponds to the "observation mode" of the present invention. Therefore, the first special mode corresponds to the "first observation mode" of the present invention, and the second special mode corresponds to the "second observation mode" of the present invention.

A mode operation unit is provided in the image processing unit 110 of Embodiment 3D. The mode operation unit selects one of the first special mode and the second special mode, and sets the priority of the blood vessel index value, which is used in the case of generating the emphasized image, in the selected special mode. The priority is set for each blood vessel index value based on diagnostics.

In Embodiment 3D, the priority of each abnormal index value stored in the abnormal index value priority table 102 is set based on the priority set by the mode operation unit. Then, in a case where the first special mode is changed to the second special mode as the observation conditions, the priority changing unit 112 changes the type of the abnormal index value stored in the abnormal index value priority table 102 to the type of the abnormal index value used in the second special mode. In addition, the priority changing unit 112 changes the priority, which is set for each abnormal index value in the abnormal index value priority table 102, based on the priority of each blood vessel index value set in the second special mode. In this manner, in a case where the special mode is changed, the priority is changed. Therefore, even in a case where the priority of the blood vessel index value that are to be noticed differs depending on the special mode, it is possible to display the color by narrowing down the range to blood vessel index values having high priorities after the change.

Embodiment 3E

In Embodiment 3E, the priority changing unit 112 changes the priority as described above in a case where a specific coloring agent is sprayed on the observation target as the observation conditions. In a case where a specific coloring agent is sprayed on the observation target, almost all of the endoscope image (for example, ¾ or more of the endoscope image) are expressed by a color different from the original color of the observation target. Therefore, the priority changing unit 112 analyzes the color of the endoscope image, and changes the priority in a case where it is recognized that a specific coloring agent has been sprayed on the observation target based on the color. For example, assuming that the priority of the density of blood vessels stored in the abnormal index value priority table 102 before spraying a coloring agent is "high", in a case where the coloring agent is sprayed, the priority changing unit 112 changes the priority of the density of blood vessels stored in the abnormal index value priority table 102 to "medium". Based on the input operation of the console 19, it may be possible to recognize whether or not a specific coloring agent has been sprayed on the observation target. In this manner, in a case where a coloring agent is sprayed, the priority is changed. Therefore, even in a case where the priority of the blood vessel index value that are to be noticed differs depending on the presence or absence of a coloring agent, it is possible to display the color by narrowing down the range to blood vessel index values having high priorities after the change.

Embodiment 3F

The image processing unit 110 of Embodiment 3F has a distance acquisition unit. The distance acquisition unit acquires a first observation distance, which is the observation distance from the observation target, and a second observation distance, which is different from the first observation distance, from the endoscope image acquired by the image acquisition unit 70.

Figure 9:
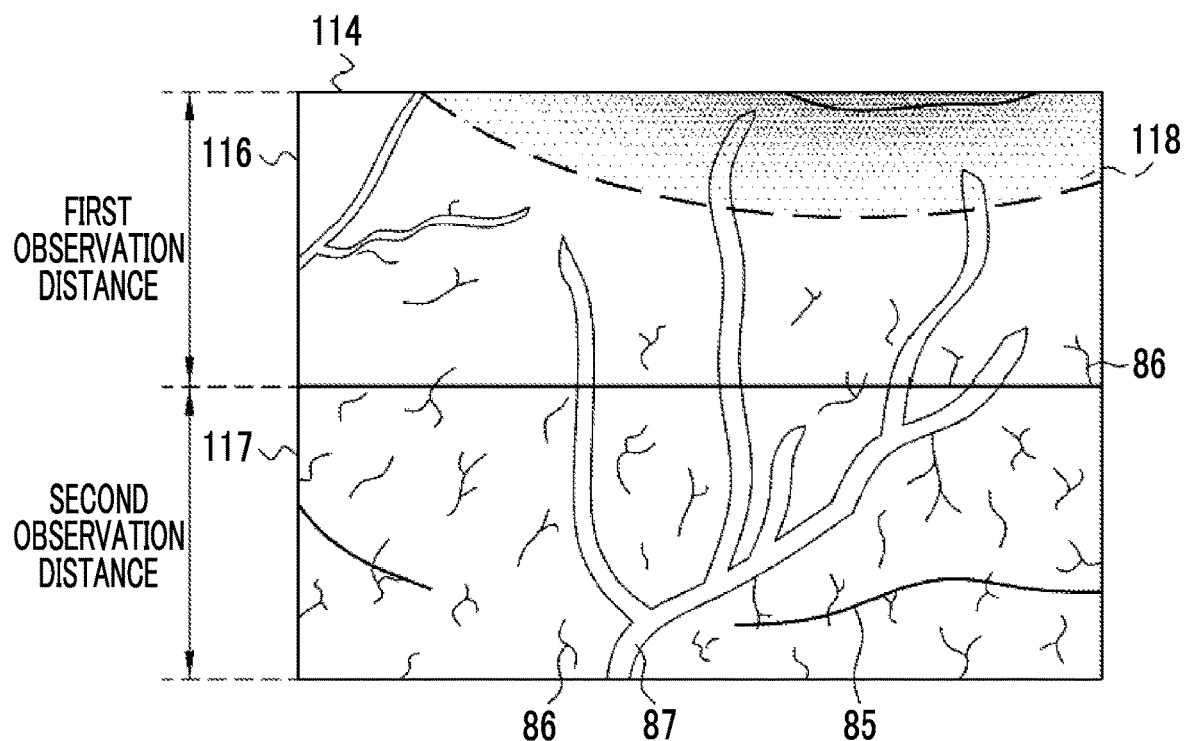
FIG. 9 is an explanatory diagram showing an endoscope image captured in a state in which an endoscope is inclined with respect to the surface of an observation target.

Specifically, the distance acquisition unit divides an endoscope image 114 shown in FIG. 9 into a first area 116 and a second area 117. The endoscope image 114 is an image captured in a state in which the endoscope 12 is inclined with respect to an axis perpendicular to the surface of the observation target, and the depth of the observation target is expressed. In the endoscope image 114, it is possible to observe the mucous membrane 85, the extremely superficial blood vessel 86, and the superficial blood vessel 87 of the observation target. In the first area 116, a dark portion 118 is present in the depth direction. In the dark portion 118, the exposure amount is equal to or less than the threshold value.

The distance acquisition unit calculates the average observation distance of the first area 116 by calculating the average exposure amount of the first area 116. The distance acquisition unit acquires the calculated average observation distance of the first area 116 as the first observation distance. Similarly, the distance acquisition unit calculates the average observation distance of the second area 117 by calculating the average exposure amount of the second area 117. The distance acquisition unit acquires the calculated average observation distance of the second area 117 as the second observation distance. The average exposure amount in the first area 116 including the dark portion 118 is smaller than that in the second area 117. Therefore, the first observation distance is a longer distance than the second observation distance. For this reason, the distance acquisition unit can estimate the angle of the endoscope 12 based on the distribution of the exposure amount in the endoscope image.

In a case where the distance acquisition unit acquires the first observation distance and the second observation distance as the observation conditions, the priority changing unit 112 changes the priority as described above. For example, in the first area 116, the priority changing unit 112 changes the priority of the density of blood vessels stored in the abnormal index value priority table 102 from "high" to "low". In the second area 117, the priority changing unit 112 changes the priority of the depth of the blood vessel stored in the abnormal index value priority table 102 from "low" to "high". In this manner, in a case where different observation distances within the endoscope image are obtained, the priority is changed. Therefore, even in a case where the priority of the blood vessel index value that are to be noticed differs depending on the observation distance, it is possible to display the color by narrowing down the range to blood vessel index values having high priorities after the change.

Fourth Embodiment

In each of the embodiments described above, the extremely superficial observation image 82 or the superficial observation image 83 is used as the brightness information of the emphasized image. However, a difference value between the normal blood vessel index value and the abnormal blood vessel index value may be used. Hereinafter, a case will be described in which a difference value between the normal blood vessel index value and the abnormal blood vessel index value is used as brightness information.

Figure 10:
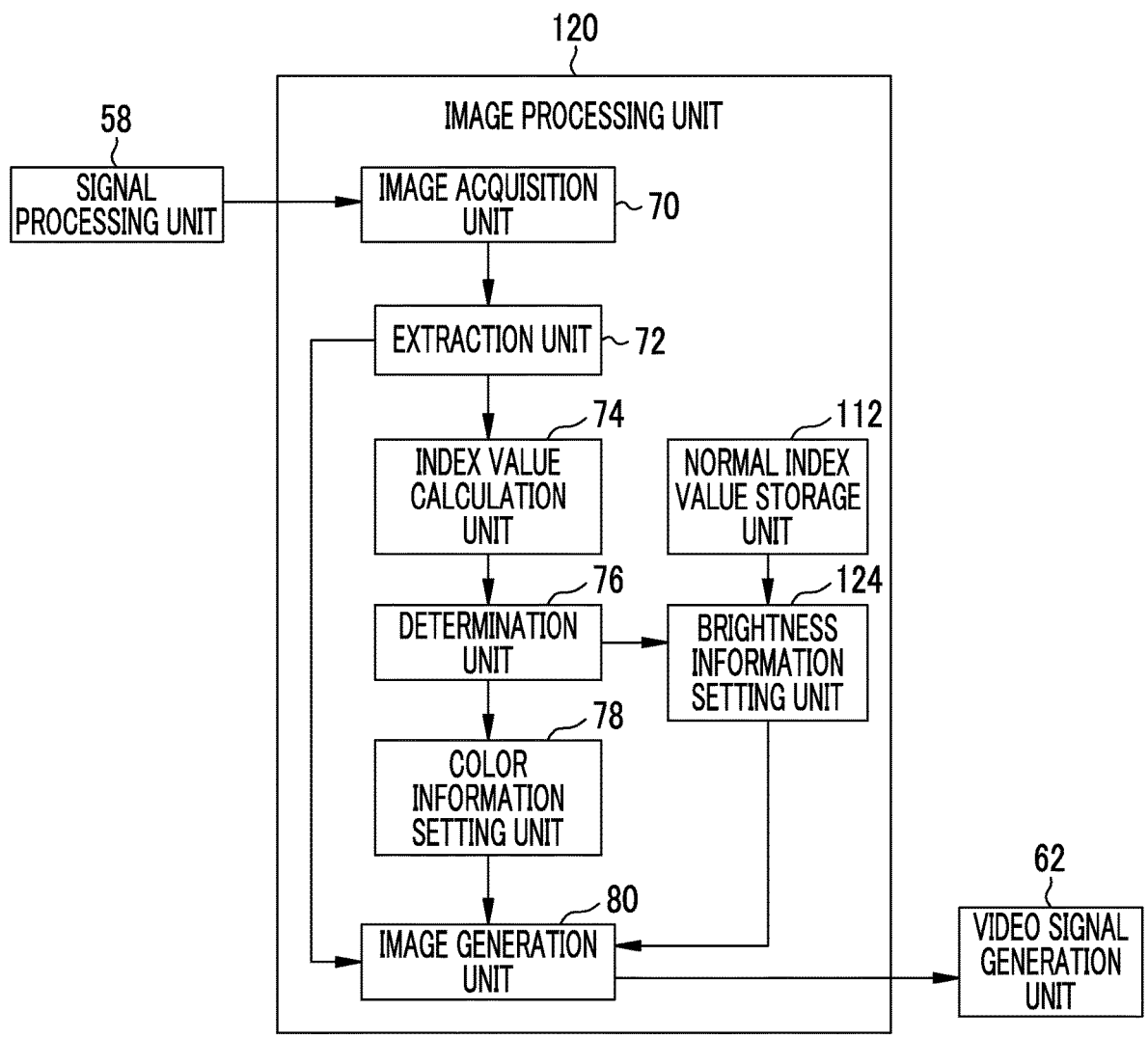
FIG. 10 is a block diagram showing a function of an image processing unit of a fourth embodiment.

In a fourth embodiment, instead of the image processing unit 60 of the first embodiment described above, an image processing unit 120 shown in FIG. 10 is provided.

In addition to each component of the image processing unit 60 of the first embodiment described above, the image processing unit 120 has a normal index value storage unit 122 and a brightness information setting unit 124. The normal index value storage unit 122 stores a normal index value. The normal index value is a normal blood vessel index value indicating a normal state with respect to the abnormal index value.

The brightness information setting unit 124 divides the endoscope image into a plurality of regions, and calculates a difference value between the abnormal index value and the normal index value for each of the divided regions. Specifically, abnormal index values of pixels in a region are averaged, and a difference value between the averaged abnormal index value and the normal index value is calculated. Since the abnormal index value is apart from the normal index value as the difference value increases, deterioration of the lesion in the region is serious. The division of the endoscope image may be performed based on the console 19.

The brightness information setting unit 124 sets brightness information according to the calculated difference value. For example, the brightness information setting unit 124 sets the brightness information based on the position of the difference value on the Y axis in the YCbCr space. Specifically, the brightness information setting unit 124 associates the difference value with the Y axis, determines the position of the difference value on the Y axis based on the difference value, and sets the Y value at the position as brightness information. The brightness information setting unit 124 sets the brightness to be higher as the difference value becomes larger.

The image generation unit 80 generates an emphasized image based on the color information set by the color information setting unit 78 and the brightness information set by the brightness information setting unit 124. In the emphasized image in this case, pixels having abnormal index values are not only colored with colors based on the color information, but also expressed with brightness based on the difference value between the abnormal index value and the normal index value. Therefore, the emphasized image becomes dark in a case where the deterioration of the lesion is relatively minor, and becomes bright in a case where the deterioration of the lesion is serious. Thus, among blood vessel index values that are to be noticed, a blood vessel index value having a large difference from the normal value is displayed with high brightness. As a result, it is possible to present a more useful blood vessel index value.

Figure 11:
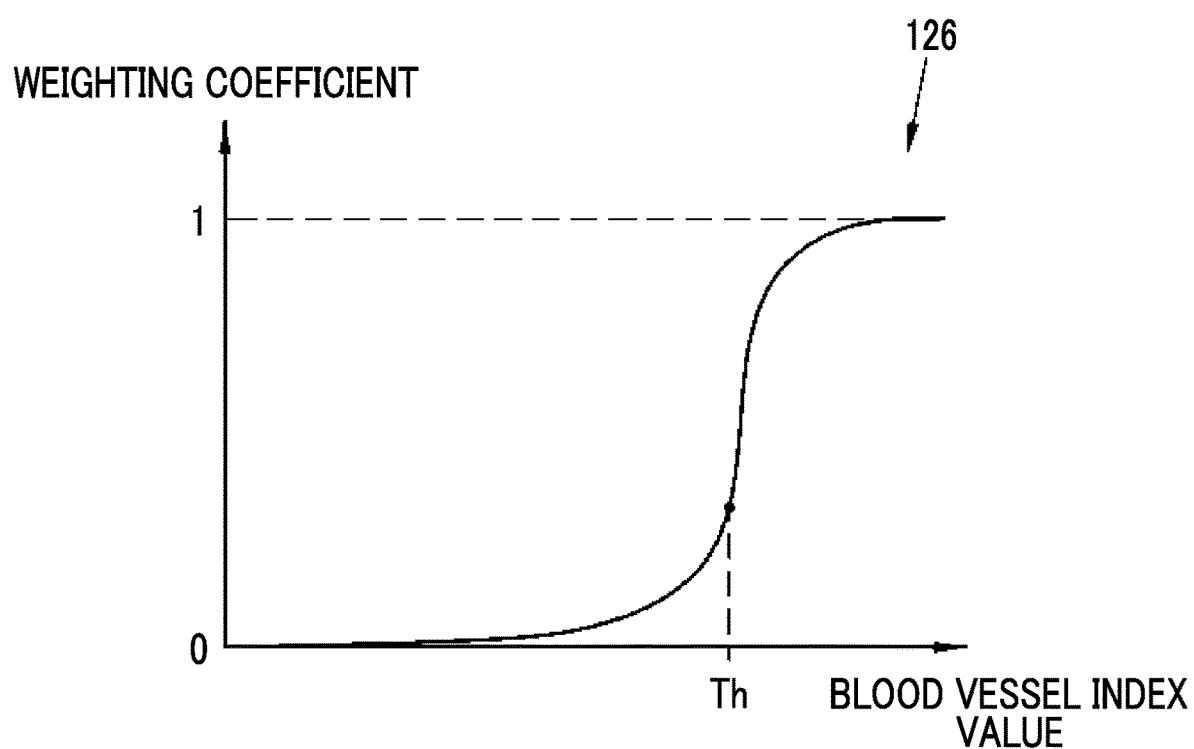
FIG. 11 is an explanatory diagram illustrating a two-dimensional LUT used for the setting of color information.

In each of the embodiments described above, the color information setting unit 78 sets color information for the abnormal index value using the YCbCr space. However, the color information may be set with reference to a two-dimensional LUT 126 shown in FIG. 11. In the two-dimensional LUT 126, for example, the vertical axis indicates a weighting coefficient and the horizontal axis indicates a blood vessel index value. The weighting coefficient is, for example, a numerical value greater than 0 and equal to or less than 1. In the two-dimensional LUT 126, it is assumed that, for example, in a case where the blood vessel index value becomes equal to or greater than a threshold value Th, the value of the weighting coefficient changes more greatly than in a case where the blood vessel index value is less than the threshold value Th. Then, in the case of assigning the blood vessel extraction image 84 to the color difference channels Cb and Cr, the image generation unit 80 multiplies the weighting coefficient based on the two-dimensional LUT 126 from the color information setting unit 78. At the time of this assignment, a specific coefficient may be further multiplied. In this manner, even in a case where a plurality of blood vessel index values are used, the color is displayed by narrowing down the range to blood vessel index values that are to be noticed. As a result, it is possible to assist the doctor to quickly perform determination upon diagnosis.

In the two-dimensional LUT 126, in a case where the blood vessel index value is less than the threshold value Th, the image generation unit 80 does not have to change the color of the blood vessel. In the two-dimensional LUT, the value of the weighting coefficient may increase in proportion to the blood vessel index value.

In each of the embodiments described above, the determination unit 76 determines whether the blood vessel index value is a normal value or an abnormal value using a specific threshold value. However, instead of this, the determination unit 76 may perform the determination using a look-up table for determination. The look-up table for determination stores to which of the normal value and the abnormal value the blood vessel index value corresponds. For example, the look-up table for determination stores to which of the normal value and the abnormal value the density of blood vessels corresponds. Then, the determination unit 76 determines whether the density of blood vessels calculated by the index value calculation unit 74 is a normal value or an abnormal value with reference to the look-up table for determination.

In addition to performing the determination using a specific threshold value or the look-up table for determination, the determination unit 76 may perform the determination using a two-dimensional map including two axes. For example, in the two-dimensional map, the determination unit 76 associates the density of blood vessels with one axis, and associates the number of branches of a blood vessel with the other axis. On the two-dimensional map, a region to which the density of a normal value and the number of branches of a normal value belong, a region to which the density of an abnormal value and the number of branches of an abnormal value belong, a region to which the density of a normal value and the number of branches of an abnormal value belong, and a region to which the density of an abnormal value and the number of branches of a normal value belong are set. The determination unit 76 determines whether each of the density of blood vessels and the number of branches is a normal value or an abnormal value according to the region to which the density of blood vessels and the number of branches calculated by the index value calculation unit 74 belong. The determination may be performed using a three-dimensional map including three axes. In the case of the three-dimensional map, three different blood vessel index values can be associated with the respective axes.

In each of the embodiments described above, the image generation unit 80 performs processing for emphasizing the region of the abnormal index value. However, instead of this, the region of the abnormal index value may be relatively emphasized by performing processing for suppressing regions other than the region of the abnormal index value.

In each of the embodiments described above, the color information setting unit sets the color information for the abnormal index value. However, instead of this, the color information setting unit may set the color information for the normal index value. In the case of setting the color information for the normal index value, it is possible to use the same method as in the case of setting the color information for the abnormal index value. Therefore, the detailed explanation thereof will be omitted. In this case, for example, the image generation unit may generate an emphasized image by coloring pixels, which have blood vessel index values determined to be normal values by the determination unit, based on the color information without coloring pixels having abnormal index values.

In each of the embodiments described above, the image processing unit emphasizes blood vessels. However, in addition to or instead of this, lymphatic vessels may be emphasized. Lymphatic vessels are stretched throughout the body along the blood vessels. For this reason, in a case where cancer cells invade into lymphatic vessels, there is a risk of metastasis to lymphatic nodes or other organs through the lymphatic vessels. Therefore, by emphasizing not only blood vessels but also lymphatic vessels, the doctor can determine cancer metastasis. In addition, other tubular structures and the like may be emphasized without being limited to the blood vessels or the lymphatic vessels.

In the embodiments described above, the LEDs 20a to 20d of four colors are used. However, instead of the LEDs 20a to 20d of four colors, the observation target may be illuminated using a broadband light source, such as a xenon lamp, and a rotary filter. In addition, the observation target may be imaged using a monochrome imaging sensor instead of the color imaging sensor 38. Others are the same as in the first embodiment.

Figure 12:
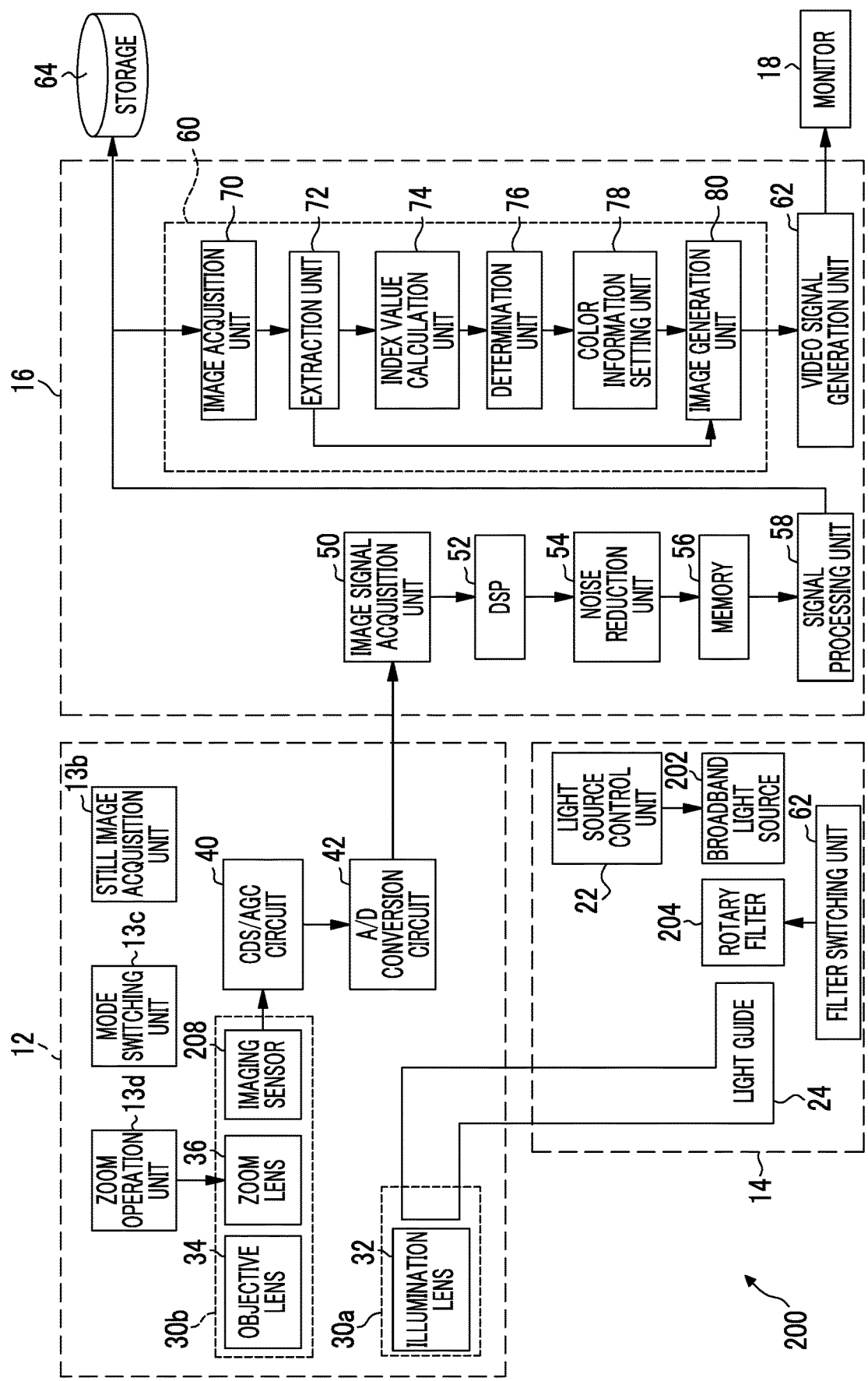
FIG. 12 is a block diagram of a function of an endoscope system including a broadband light source and a rotary filter.

In an endoscope system 200 shown in FIG. 12, instead of the LEDs 20a to 20d of the endoscope system 10, a broadband light source 202, a rotary filter 204, and a filter switching unit 206 are provided in the light source device 14. In addition, instead of the color imaging sensor 38, a monochrome imaging sensor 208 in which no color filter is provided is provided in the imaging optical system 30b.

The broadband light source 202 is a xenon lamp, a white LED, or the like, and emits white light having a wavelength range from blue to red. The rotary filter 204 includes a normal mode filter 210 provided on the inner side close to the rotation axis and a special mode filter 212 provided on the outer side far from the rotation axis (refer to FIG. 13). The filter switching unit 206 moves the rotary filter 204 in the radial direction. Specifically, the filter switching unit 206 inserts the normal mode filter 210 of the rotary filter 204 into the optical path of white light in a case where the normal mode is set by the mode switching unit 13c, and inserts the special mode filter 212 of the rotary filter 204 into the optical path of white light in a case where the special mode is set.

Figure 13:
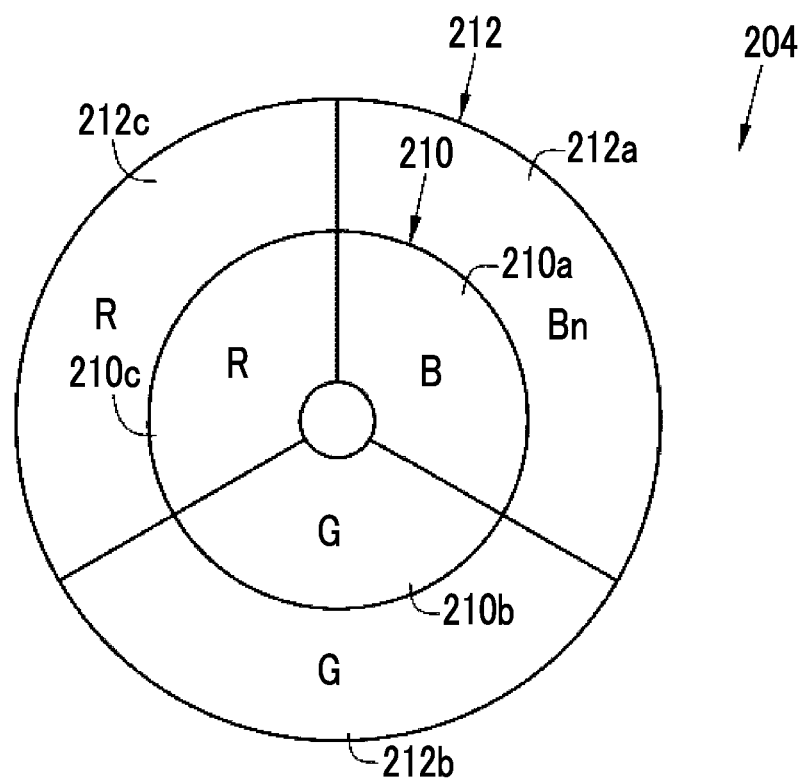
FIG. 13 is a plan view of a rotary filter.

As shown in FIG. 13, a B filter 210a, a G filter 210b, and an R filter 210c are provided along the circumferential direction in the normal mode filter 210. The B filter 210a transmits blue light of the white light. The G filter 210b transmits green light of the white light. The R filter 210c transmits red light of the white light. Therefore, at the time of normal mode, the rotary filter 204 rotates to alternately illuminate the observation target with blue light, green light, and red light.

In the special mode filter 212, at least a filter that transmits narrowband light having a specific wavelength range of the white light is provided is provided along the circumferential direction. A Bn filter 212a, a G filter 212b, and an R filter 212c are provided in the special mode filter 212. The Bn filter 212a transmits blue narrowband light having a specific wavelength range of the white light. The G filter 212b transmits green light of the white light. The R filter 212c transmits red light of the white light. Therefore, at the time of special mode, the rotary filter 204 rotates to alternately illuminate the observation target with blue narrowband light, green light, and red light.

In the special mode filter 212, in addition to the above-described filters 212a to 212c, a V filter that transmits violet light of the white light, a B filter that transmits blue light of the white light, and the like may be provided. As in the first embodiment described above, in the case of sequentially emitting the violet light V and the blue light B in the special mode, the V filter and the B filter are provided in the special mode filter 212.

In the endoscope system 200, at the time of normal mode, the monochrome imaging sensor 208 images the observation target every time the observation target is illuminated with the blue light, the green light, and the red light. As a result, image signals of three colors of RGB can be obtained. Then, a normal observation image is generated based on the image signals of RGB colors by the same method as in the first embodiment described above.

On the other hand, at the time of special mode, the monochrome imaging sensor 208 images the observation target every time the observation target is illuminated with the blue narrowband light, the green light, and the red light. As a result, a Bn image signal, a G image signal, and an R image signal can be obtained. Then, a special observation image is generated based on the Bn image signal, the G image signal, and the R image signal by the same method as in the first embodiment. In the endoscope system 200, blood vessels of the observation target are extracted from the special observation image, a plurality of blood vessel index values are calculated for the extracted blood vessels, it is determined whether each of the blood vessel index values is a normal value or an abnormal value, color information is set for an abnormal index value that is a blood vessel index value determined to be an abnormal value or color information is set for a normal index value that is a blood vessel index value determined to be a normal value, and an emphasized image is generated based on the color information.

Figure 14:
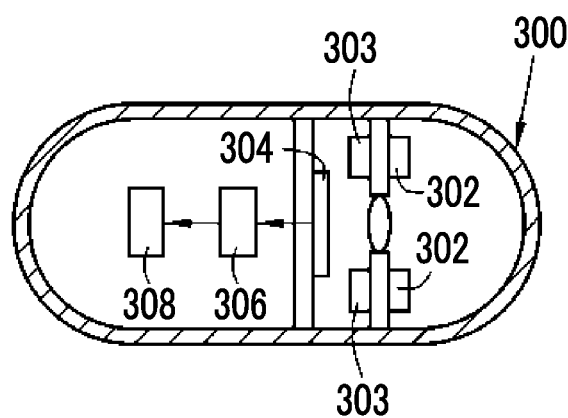
FIG. 14 is a schematic diagram of a capsule endoscope.

In each embodiment described above, the present invention is implemented by the endoscope systems 10 and 200 in which the endoscope 12 including the imaging sensor 38 is inserted into the subject to observe the inside of the subject. However, the present invention may also be implemented in a capsule endoscope system. For example, the capsule endoscope system includes at least a capsule endoscope 300 shown in FIG. 14 and a processor device (not shown). The capsule endoscope 300 includes a light source 302, a light source control unit 303, an imaging sensor 304, an image signal acquisition processing unit 306, and a transmitting and receiving antenna 308. The light source 302 is configured similarly to the light source 20 of the endoscope system 10, and emits illumination light under the control of the light source control unit 303. The image signal acquisition processing unit 306 functions as the image signal acquisition unit 50, the DSP 52, the noise reduction unit 54, and the signal processing unit 58. The processor device of the capsule endoscope system is configured similarly to the processor device 16 of the endoscope system 10, and also functions as the image processing unit 60. The endoscope image generated by the image signal acquisition processing unit 306 is transmitted to the processor device through the transmitting and receiving antenna 308. In the processor device, blood vessels of the observation target are extracted from the received endoscope image, a plurality of blood vessel index values are calculated for the extracted blood vessels, it is determined whether each of the blood vessel index values is a normal value or an abnormal value, color information is set for an abnormal index value that is a blood vessel index value determined to be an abnormal value or color information is set for a normal index value that is a blood vessel index value determined to be a normal value, and an emphasized image is generated based on the color information.

EXPLANATION OF REFERENCES 10, 200: endoscope system
12: endoscope
12a: insertion part
12b: operation unit
12c: bending portion
12d: distal end portion 13a: angle knob
13b: still image acquisition unit
13c: mode switching unit
13d: zoom operation unit
14: light source device
16: processor device
18: monitor
19: console
20: light source
20a: V-LED
20b: B-LED
20c: G-LED
20d: R-LED
22: light source control unit
24: light guide
30a: illumination optical system
30b: imaging optical system
32: illumination lens
34: objective lens
36: zoom lens
38: imaging sensor
40: CDS/AGC circuit
42: A/D conversion circuit
50: image signal acquisition unit
52: DSP
54: noise reduction unit
56: memory
58: signal processing unit
60, 110, 120: image processing unit
62: video signal generation unit
64: storage
70: image acquisition unit
72: extraction unit
74: index value calculation unit
76: determination unit
78, 100: color information setting unit
80: image generation unit
82: extremely superficial observation image
83: superficial observation image
84: blood vessel extraction image
85: mucous membrane
86: extremely superficial blood vessel
87: superficial blood vessel
94: emphasized image
102: abnormal index value priority table
104: color information priority table
112: priority changing unit
114: endoscope image
116: first area
117: second area
118: dark portion
122: normal index value storage unit
124: brightness information setting unit
126: two-dimensional LUT
202: broadband light source
204: rotary filter
206: filter switching unit
208: monochrome imaging sensor
210: normal mode filter
210a: B filter
210b: G filter
210c: R filter
212: special mode filter
212a: Bn filter
212b: G filter
212c: R filter
300: capsule endoscope
302: light source
303: light source control unit
304: imaging sensor
306: image signal acquisition processing unit
308: transmitting and receiving antenna

What is claimed is:

1. An endoscope system, comprising:
a processor configured to function as:
 an image acquisition unit that acquires an image obtained by imaging an observation target with an endoscope;
 an extraction unit that extracts a structure included in the observation target from the image;
 an index value calculation unit that calculates a plurality of index values based on the structure extracted by the extraction unit;
 a determination unit that determines whether each of the plurality of index values is a normal value indicating a normal state or an abnormal value different from the normal value;
 a color information setting unit that sets color information for an abnormal index value, which is the index value determined to be the abnormal value by the determination unit, or sets color information for a normal index value, which is the index value determined to be the normal value by the determination unit;
 an image generation unit that generates an emphasized image, in which the structure is emphasized, based on the color information set by the color information setting unit,
 a priority changing unit that changes a priority set for each of the abnormal index values or the normal index values based on observation conditions, and
 an endoscope identification unit that identifies whether the endoscope is an upper observation endoscope or a lower observation endoscope,
  wherein the color information is a plurality of pieces of information, and a priority is set for each of the pieces of color information,
 there are a plurality of the abnormal index values or a plurality of the normal index values, and a priority is set between each of the plurality of abnormal index values or between each of the plurality of normal index values,
 the color information setting unit assigns the color information having a higher priority to the abnormal index value or the normal index value having a higher priority among the abnormal index values or the normal index values,
 wherein the color information setting unit performs the assignment according to a changed priority, and
 wherein in a case where replacement between the upper observation endoscope and the lower observation endoscope is performed as the observation conditions, the priority changing unit changes a priority of each of the abnormal index values or the normal index values.

2. The endoscope system according to claim 1, wherein the determination unit performs the determination by comparing the index value with a specific threshold value, or performs the determination with reference to a look-up table that stores to which of the normal value and the abnormal value the index value corresponds.

3. The endoscope system according to claim 1, wherein the structure is a blood vessel.

4. The endoscope system according to claim 1,
wherein in a case where an observation distance from the observation target is changed from a first observation distance to a second observation distance different from the first observation distance as the observation conditions, the priority changing unit changes a priority of each of the abnormal index values or the normal index values.

5. The endoscope system according to claim 1, the processor further configured to function as:
a zoom operation unit that changes a zoom magnification of the endoscope between a first zoom magnification and a second zoom magnification different from the first zoom magnification,
wherein in a case where the first zoom magnification is changed to the second zoom magnification as the observation conditions, the priority changing unit changes a priority of each of the abnormal index values or the normal index values.

6. The endoscope system according to claim 1, the processor further configured to function as:
a mode operation unit that selects one observation mode from a plurality of observation modes in which two or more of the plurality of index values are used and sets a priority based on diagnostics for each of the index values used in the selected observation mode,
wherein a priority is set for each of the abnormal index values or the normal index values based on the priority set for each of the index values, and
in a case where the observation mode is switched from a first observation mode to a second observation mode different from the first observation mode as the observation conditions, the priority changing unit changes a priority of each of the abnormal index values or the normal index values.

7. The endoscope system according to claim 1,
wherein in a case where a specific coloring agent is sprayed on the observation target as the observation conditions, the priority changing unit changes a priority of each of the abnormal index values or the normal index values.

8. The endoscope system according to claim 1, the processor further configured to function as:
a normal index value storage unit that stores the normal index value; and
a brightness information setting unit that calculates a difference value between the abnormal index value and the normal index value and sets brightness information according to the difference value,
wherein the image generation unit generates the emphasized image based on the set color information and the set brightness information.

9. An operation method of an endoscope system, comprising:
a step in which an image acquisition unit acquires an image obtained by imaging an observation target with an endoscope;
a step in which an extraction unit extracts a structure included in the observation target from the image;
a step in which an index value calculation unit calculates a plurality of index values based on the structure extracted by the extraction unit;
a step in which a determination unit determines whether each of the plurality of index values is a normal value indicating a normal state or an abnormal value different from the normal value;
a step in which a color information setting unit sets color information for an abnormal index value, which is the index value determined to be the abnormal value by the determination unit, or sets color information for a normal index value, which is the index value determined to be the normal value by the determination unit;
a step in which an image generation unit generates an emphasized image, in which the structure is emphasized, based on the color information set by the color information setting unit,
a step in which a priority changing unit changes a priority set for each of the abnormal index values or the normal index values based on observation conditions, and
a step in which an endoscope identification unit identifies whether the endoscope is an upper observation endoscope or a lower observation endoscope,
wherein the color information is a plurality of pieces of information, and a priority is set for each of the pieces of color information,
there are a plurality of the abnormal index values or a plurality of the normal index values, and a priority is set between each of the plurality of abnormal index values or between each of the plurality of normal index values, and
the color information setting unit assigns the color information having a higher priority to the abnormal index value or the normal index value having a higher priority among the abnormal index values or the normal index values,
wherein a processor is configured to function as the image acquisition unit, the extraction unit the index value calculation unit, the determination unit, the color information setting unit, and the image generation unit,
wherein the color information setting unit performs the assignment according to a changed priority, and
wherein in a case where replacement between the upper observation endoscope and the lower observation endoscope is performed as the observation conditions, the priority changing unit changes a priority of each of the abnormal index values or the normal index values.

10. The operation method of an endoscope system according to claim 9,
wherein the determination unit performs the determination by comparing the index value with a specific threshold value, or performs the determination with reference to a look-up table that stores to which of the normal value and the abnormal value the index value corresponds.

* * * * *